(12) United States Patent
Ottery

(10) Patent No.: US 8,822,015 B1
(45) Date of Patent: Sep. 2, 2014

(54) ELASTIC COMPOSITE HAVING DUAL ELASTICIZED REGIONS, AND A SYSTEM AND METHOD FOR MAKING THE ELASTIC COMPOSITE

(75) Inventor: Trenton Ottery, Delaware, OH (US)

(73) Assignee: Associated Hygienic Products LLC, Duluth, GA (US)

( * ) Notice: Subject to any disclaimer, the term of this patent is extended or adjusted under 35 U.S.C. 154(b) by 729 days.

(21) Appl. No.: 12/069,928

(22) Filed: Feb. 14, 2008

Related U.S. Application Data

(60) Provisional application No. 60/901,446, filed on Feb. 15, 2007.

(51) Int. Cl.
*B32B 3/00* (2006.01)

(52) U.S. Cl.
USPC ........................................... 428/190

(58) Field of Classification Search
USPC ......... 428/190, 189, 192, 105, 107, 109, 112, 428/114; 604/385.27, 385.24, 385.3, 604/385.22
See application file for complete search history.

(56) References Cited

U.S. PATENT DOCUMENTS

| | | |
|---|---|---|
| 1,195,949 A | 8/1916 | Carney |
| 2,718,254 A | 9/1955 | Carlson |
| 2,901,395 A | 9/1959 | Hirschy et al. |
| 3,041,230 A | 9/1962 | Diehl |
| 3,627,621 A | 12/1971 | Mowers |
| 3,800,796 A | 4/1974 | Jacob |
| 3,801,401 A | 4/1974 | Cope et al. |
| 4,284,454 A | 8/1981 | Joa |
| 4,527,990 A | 7/1985 | Sigl |
| 4,642,151 A | 2/1987 | Coenen |
| 4,726,874 A | 2/1988 | VanVliet |
| 5,127,981 A | 7/1992 | Straub et al. |
| 5,242,436 A | 9/1993 | Weil et al. |
| 5,246,433 A | 9/1993 | Hasse et al. |
| 5,370,634 A | 12/1994 | Ando et al. |

(Continued)

FOREIGN PATENT DOCUMENTS

| | | |
|---|---|---|
| EP | 1 188 427 | 3/2002 |
| EP | 1 520 569 | 4/2005 |

(Continued)

OTHER PUBLICATIONS

International Preliminary Report on Patentability issued Jan. 6, 2009, during the prosecution of International Application No. PCT/US2007/71898. Published Jan. 6, 2009.

(Continued)

*Primary Examiner* — Catherine A Simone
(74) *Attorney, Agent, or Firm* — Fulbright & Jaworski LLP

(57) ABSTRACT

This elastic composite includes a base layer having a pair of side edges and a longitudinal centerline spaced inwardly from the side edges, and a first elastic construction supported by the base layer. The first elastic construction includes a first plurality of spaced apart elastic elements and a first top layer extending over the first elastic construction. The elastic composite also includes a second elastic construction supported by the base layer. The second elastic construction includes a second plurality of spaced apart elastic elements and a second top layer extending over the elastic construction. The first and second top layers are spaced apart and the first and second elastic constructions are spaced apart, so as to define a central non-elasticized region between the first and second elastic constructions.

11 Claims, 18 Drawing Sheets

(56) References Cited

U.S. PATENT DOCUMENTS

| | | | |
|---|---|---|---|
| 5,383,871 A | 1/1995 | Carlin et al. | |
| 5,429,694 A | 7/1995 | Herrmann | |
| 5,464,401 A | 11/1995 | Hasse et al. | |
| 5,531,729 A | 7/1996 | Coles et al. | |
| 5,531,850 A | 7/1996 | Herrmann | |
| 5,540,796 A | 7/1996 | Fries | |
| 5,591,152 A | 1/1997 | Buell et al. | |
| 5,628,741 A | 5/1997 | Buell et al. | |
| 5,669,897 A | 9/1997 | Lavon et al. | |
| 5,685,873 A | 11/1997 | Bruemmer | |
| 5,779,691 A | 7/1998 | Schmitt | |
| 5,807,368 A | 9/1998 | Helmer | |
| 5,807,371 A | 9/1998 | Toyoda et al. | |
| 5,916,207 A | 6/1999 | Toyoda et al. | |
| 5,938,652 A | 8/1999 | Sauer | |
| 6,004,306 A | 12/1999 | Robles et al. | |
| 6,086,571 A | 7/2000 | Guevara et al. | |
| 6,123,694 A | 9/2000 | Pieniak et al. | |
| 6,146,369 A | 11/2000 | Hartman et al. | |
| 6,306,122 B1 * | 10/2001 | Narawa et al. | 604/385.3 |
| 6,313,372 B1 | 11/2001 | Suzuki | |
| 6,336,922 B1 | 1/2002 | VanGompel et al. | |
| 6,340,782 B1 | 1/2002 | Kling et al. | |
| 6,419,667 B1 | 7/2002 | Avalon et al. | |
| 6,425,430 B1 | 7/2002 | Ward et al. | |
| 6,454,750 B1 | 9/2002 | Vogt et al. | |
| 6,454,752 B1 | 9/2002 | Huang et al. | |
| 6,572,595 B1 | 6/2003 | Klemp et al. | |
| 6,649,001 B2 | 11/2003 | Heden et al. | |
| 6,855,223 B2 | 2/2005 | Johnson | |
| 7,361,246 B2 | 4/2008 | Chang et al. | |
| 7,462,172 B2 | 12/2008 | Wright et al. | |
| 2001/0039700 A1 | 11/2001 | Krueger | |
| 2002/0002358 A1 | 1/2002 | Durrance et al. | |
| 2002/0038110 A1 | 3/2002 | Kusibojoska et al. | |
| 2002/0049421 A1 * | 4/2002 | Hayase et al. | 604/385.27 |
| 2002/0151863 A1 * | 10/2002 | Toyoshima | 604/385.29 |
| 2002/0177829 A1 | 11/2002 | Fell et al. | |
| 2003/0064652 A1 | 4/2003 | Heden et al. | |
| 2003/0069557 A1 | 4/2003 | Driskell et al. | |
| 2003/0083634 A1 | 5/2003 | Fernfors | |
| 2003/0089454 A1 | 5/2003 | Johnson | |
| 2003/0109844 A1 | 6/2003 | Gibbs | |
| 2003/0139725 A1 | 7/2003 | Gibbs | |
| 2003/0144643 A1 | 7/2003 | Jarpenberg et al. | |
| 2004/0039363 A1 * | 2/2004 | Sugiyama et al. | 604/385.101 |
| 2004/0243090 A1 | 12/2004 | Toyoshima et al. | |
| 2005/0095942 A1 | 5/2005 | Mueller et al. | |
| 2005/0131373 A1 * | 6/2005 | Wright et al. | 604/385.27 |
| 2006/0058767 A1 | 3/2006 | Zhang et al. | |
| 2006/0058768 A1 | 3/2006 | Zhang et al. | |
| 2006/0241560 A1 | 10/2006 | Chang et al. | |
| 2007/0016155 A1 | 1/2007 | Chang et al. | |
| 2009/0124992 A1 | 5/2009 | Chang et al. | |

FOREIGN PATENT DOCUMENTS

| | | |
|---|---|---|
| JP | 2002-192641 | 7/2002 |
| WO | WO-9519258 | 7/1995 |
| WO | WO-01/00915 | 1/2001 |
| WO | WO-0232364 | 4/2002 |
| WO | WO-/03/041627 | 5/2003 |
| WO | WO-03017903 | 6/2003 |
| WO | PCT/US04/12832 | 4/2004 |
| WO | WO-2004/087416 | 10/2004 |
| WO | WO-2005060910 | 7/2005 |

OTHER PUBLICATIONS

International Search Report issued Jul. 8, 2008, during the prosecution of international Application No. PCT/US2007/71898. Published Oct. 9, 2008.

Written Opinion issued Jul. 8, 2008, during the prosecution of International Application No. PCT/US2007/71898. Published Dec. 26, 2008.

Nonfinal Office Action mailed Jan. 27, 2006, during the prosecution of U.S. Appl. No. 10/733,649.

Final Office Action mailed Sep. 15, 2006, during the prosecution of U.S. Appl. No. 10/733,649.

Nonfinal Office Action mailed Jun. 8, 2007, during the prosecution of U.S. Appl. No. 10/733,649.

Nonfinal Office Action mailed Dec. 26, 2007, during the prosecution of U.S. Appl. No. 10/733,649.

International Preliminary Report on patentability mailed Jun. 22, 2006, during the prosecution of international Application No. PCT/US2004/012832.

International Search Report mailed Oct. 1, 2004, during the prosecution of International Application No. PCT/US2004/012832. Published Jul. 7, 2005.

Written Opinion mailed Oct. 1, 2004, during the prosecution of International Application No. PCT/US2004/012832. Published Jul. 7, 2005.

Nonfinal Office Action mailed Jun. 16, 2008, during the prosecution of U.S. Appl. No. 11/474,653.

Nonfinal Office Action mailed Sep. 19, 2007, during the prosecution of U.S. Appl. No. 11/113,114.

Final Office Action mailed Mar. 27, 2008, during the prosecution of U.S. Appl. No. 11/113,114.

Information Disclosure Statement from U.S. Appl. No. 12/290,006, filed Jun. 19, 2009.

* cited by examiner

ELASTIC COMPOSITE HAVING DUAL ELASTICIZED REGIONS, AND A SYSTEM AND METHOD FOR MAKING THE ELASTIC COMPOSITE

This application claims the benefit of the filing date of U.S. Provisional Application Ser. No. 60/901,446, filed on Feb. 15, 2007. The above application is hereby incorporated by reference for all purposes and made a part of the present disclosure.

BACKGROUND OF THE INVENTION

The present invention relates generally to elastic composites. More particularly, the present invention relates to an elastic composite that can be used in the manufacture of a garment, other textile or fabric structures, similar material structures, and the like, but more particularly, disposable absorbent articles and garments. The elastic composite of the present invention is well suited in providing an elastic component that can be employed in one or more areas of the disposable absorbent article. The present invention also relates to a system and method of making the elastic. The elastic composite and the system and method for making the elastic composite are particularly suited for use with or on disposable absorbent garments or articles such as baby diapers and training pants. To illustrate various aspects of the invention, exemplary and preferred embodiments are described herein in the context of disposable absorbent garments.

U.S. Pat. Nos. 7,462,172 and 7,361,246 provide background information on elastic composites (and the manufacture of such composites) of the type relevant to the present invention. Accordingly, some portions of the publications have been included herein to facilitate description of the invention. In any event, these two publications are also hereby incorporated by reference and made a part of the present disclosure, but only to the extent that incorporated subject matter provides background information and/or exemplary composites and processes suitable for use on, or with, the present inventive composites, systems, and methods. Thus, the incorporated subject matter shall not serve to limit the scope of the present invention.

Disposable absorbent garments contemplated by the invention include disposable diapers, disposable pull-on garments and training pants, and the like. These garments are worn about the lower torso or waist of the user so as to receive and contain urine and other bodily wastes. The benefits provided by the use of a disposable diaper on an infant are well known and its use has become widespread. Disposable pull-on garments include training pants, pull-on diapers, disposable underwear, and adult incontinence garments. As for training pants, these garments are used by young children to facilitate a child's transition from using diapers to wearing regular underpants (i.e., during toilet training). Training pants (and other disposable pull-on pants have closed sides such that the user or caregiver raises the garment about the user's legs to wear the garment and slips the garment downward about the user's legs to take it off.

The principal elements of a typical disposable absorbent garment include a liquid permeable inner layer (or topsheet), a liquid impermeable outer layer (or backsheet), and an absorbent core sandwiched between the inner and outer layers. Elastic members may be incorporated into different parts of the garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of a disposable absorbent garment. The resulting elastication allows the garment to stretch when it is put on and when it is worn. The elastication allows the garment to accommodate variations in waist size and leg size of the user, while fitting snugly about the waist and legs.

When elastic members are incorporated into a part or area of the garment, that part or area typically becomes a distinct, functional component of the garment. These elastic components include the side panels or ear portions, the waistband, and fastening tabs. The elastic components to which the present invention is directed are generally elongated, and may be a distinct portion of a larger, unitary piece, or a separate, attachable component. Furthermore, the elastic component typically contains one or more sections or layers in addition to the elastic members. In this regard, such an elastic component may be referred to as an elastic composite of the type which the present invention is concerned.

Due in part to its multi-component construction, these elastic composites may require a dedicated sub-process for manufacture which must be accommodated by the greater garment manufacturing process. Alternatively, the elastic composite may be manufactured independently or simply, manufactured in a separate sub-process detached from the central garment manufacturing system. In either case, a source of the elastic composite may be provided as input to the garment manufacturing process.

In most applications, the elastic composite has a significant impact on the fit and sealability of the garment, as well as the general appearance and construction quality of the garment. The design and construction of the elastic composite can also represent a significant portion of the cost of manufacturing the garment. It is, therefore, always desirable to provide a functionally and/or aesthetically improved elastic composite or a cost effective system and method of making the elastic composite.

It is contemplated that, in some applications, manufacturing elastic composite having dual elasticized regions may prove more efficient and economical than producing elastic composites having a single elasticized region (even when single elasticized elastic composites are ultimately employed). In one respect, the present invention addresses the particular technical challenge of providing dual (or multiple) elasticized regions on ari elastic composite. In another respect, the invention addresses the technical challenge of providing a system and method that is practical, efficient, and cost effective. For example, the system and method should preferably utilize commonly available components and sub-processes.

In any event, it is desirable for the target elastic composite (having dual elasticized regions), system, and method of manufacturing to be practical, and provide functional or aesthetic attributes. It is also desirable that the design and construction of the elastic composite has a minimal, if not positive, impact on the efficiency of present systems and methods. The design and construction should also have a minimal, if not positive, impact on the overall manufacturing cost of the elastic composite or the final product.

SUMMARY OF THE INVENTION

In one aspect of the present invention, an elastic composite is provided for use in manufacturing disposable absorbent garments. The elastic composite includes a base layer having a pair of side edges and a longitudinal centerline spaced inwardly from the side edges, and a first elastic construction supported by the base layer. The first elastic construction includes a first plurality of spaced apart elastic elements and a first top layer extending over the first elastic construction. The elastic composite also includes a second elastic construction supported by the base layer. The second elastic construction includes a second plurality of spaced apart elastic elements and a second top layer extending over the elastic construction. The first and second top layers are spaced apart and the first and second elastic constructions are spaced apart, so as to define a central non-elasticized region between the first and second elastic constructions. Preferably, the first elastic construction and the second elastic construction are spaced inwardly from the first side edge and the second side edge, respectively. More preferably, the first and second elastic constructions are spaced inwardly from the first and second side edges, respectively, to define first and second non-elasticized regions therebetween. In a preferred embodiment, the central non-elasticized region is a single layer, seamless construction. In further embodiments, the plurality of spaced apart elastic elements are disposed in generally parallel relation and/or distributed in a direction generally parallel with the longitudinal centerline, and/or applied in the cross-machine direction.

In another aspect of the present invention, a method is provided for making an elastic composite having dual elasticized regions. The method entails conveying a base web and integrating a first elastic sub-composite with the base web. Then, a second elastic sub-composite is integrated with the base web, whereby the second elastic sub-composite is spaced apart from the first elastic sub-composite. As a result, an elastic composite having dual elasticized regions is produced. In further embodiments, the method may include one or more additional steps involving the integration of yet another (e.g., a third) elastic sub-composite with the base web (already having dual elasticized regions). The resulting product is another elastic composite with multiple elasticized regions.

In another aspect of the present invention, a method of making an elastic composite (having dual elasticized regions) entails conveying a first web and applying elastic elements to the first web to produce a first elastic sub-composite. A base web is then conveyed and the first elastic sub-composite is integrated with the base web. A second web is conveyed and elastic elements are applied to the second web to produce a second elastic sub-composite. The second elastic sub-composite is then integrated with the base web, thereby producing an elastic composite having dual elasticized regions. In one embodiment, the steps of applying elastic elements are performed simultaneously such that the elastic elements are applied simultaneously about the first and second webs to produce two webs of first and second elastic sub-composites.

In yet another aspect of the present invention, an elastic composite is provided for use in manufacturing disposable absorbent garments. The inventive elastic composite includes a base layer and a first elastic sub-composite supported by the base layer. The first elastic sub-composite has a first plurality of spaced apart elastic elements disposed in generally parallel relation, and a top layer extending over the first plurality of elastic elements. The inventive elastic composite further includes a second elastic sub-composite supported by the base layer, the second elastic sub-composite having a second plurality of spaced apart elastic elements disposed in generally parallel relation and a top layer extending over the second plurality of elastic elements. Moreover, the first and second sub-composites are spaced apart to define a central non-elasticized region ("dead zone") therebetween. Preferably, the first and second sub-composites are spaced apart to define a seamless central non-elasticized region formed by the base layer. More preferably, the base layer includes a first side edge and a second side edge, and the first plurality of elastic elements are spaced inwardly from the first side edge to form (in addition to the central non-elasticized region) a first non-elasticized region therebetween, and the second plurality of elastic elements are spaced inwardly from the second side edge to form a second non-elasticized region therebetween.

For purposes of the present description, the term "elastic band" or "elastic composite" refers to a multi-layer construction. In this construction, a plurality of elastic members, such as threads or strands, are disposed adjacent one or more layers, e.g., backsheet and topsheet. In this way, the elastic elements impart elasticity to the adjacent layers and thus, to that part of the garment or other textile structure. Such an elastic structure may be a distinct attachable component of the garment or textile structure or may be a distinct portion or section of the garment body or textile structure or a larger, unitary component of the garment body or textile structure. As used herein, the term "elastic sub-composite" shall mean a multi-component construction combination that includes elastic elements integrated with a substrate layer. Further, an elastic sub-composite provides one component that may be integrated with other components to form the elastic composite and impart elastic properties thereto.

As used herein, the term elastic composite having multiple, or a plurality of, elasticized regions includes those having dual elasticized regions. Moreover, all elastic composites having multiple or, a plurality of elasticized regions, are defined as having at least dual elasticized regions. For example, any elastic composite having three elasticized regions will have dual elasticized regions, as long as two elasticized regions are supported and spaced apart on a substrate or base layer, and at some point in the manufacturing process, consists of the only pair of elasticized regions on the base layer or base web.

DETAILED DESCRIPTION OF THE INVENTION

Generally, the present invention relates to an elastic composite, and a system and method for making the elastic composite. More particularly, the invention is directed to an elastic composite having a pair of elasticized regions that are mutually spaced apart and physically separated. Such a pair of elastic constructions on an elastic composite may be referred to herein as "dual elasticized regions."

As described previously, various aspects of the present invention are particularly suited to or for a disposable absorbent garment, such as baby diapers and training pants. To illustrate the invention and preferred embodiments of the invention, much of the following Detail Description will be provided in the context of such disposable absorbent garments. It is contemplated that various aspects of the inventive composite, garment, system, and process may be applicable to other material structures and processes. This Detailed Description and exemplary embodiment should not, therefore, be construed as limiting the invention to the structures, configurations, methods, and processes described herein.

Figure 1:
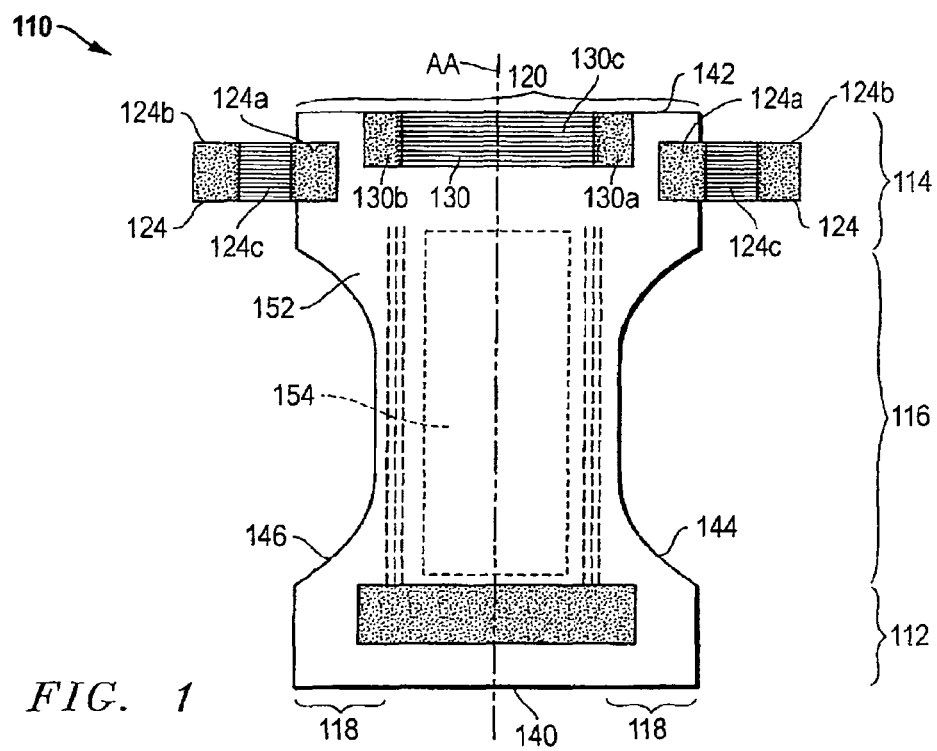
FIG. 1 is a plan view of a disposable absorbent garment in the unfolded configuration.
Figure 2A:
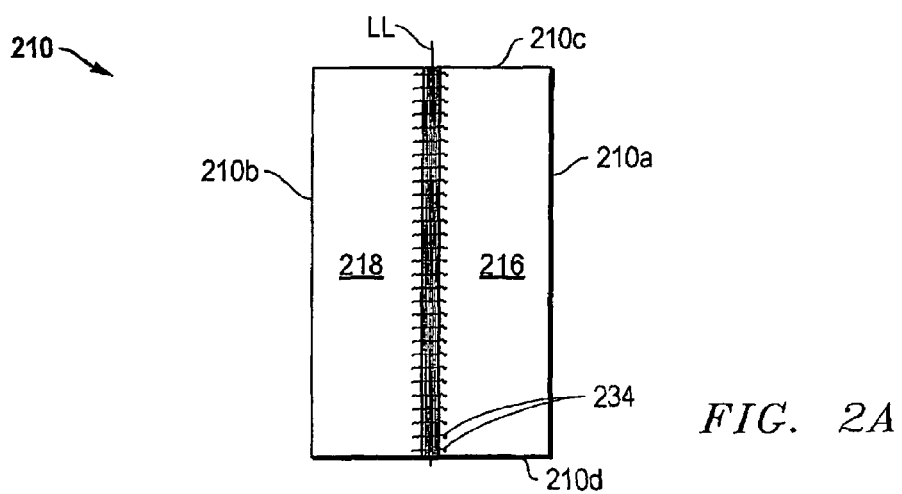
FIG. 2A is a plan view of an elastic composite.
Figure 2B:
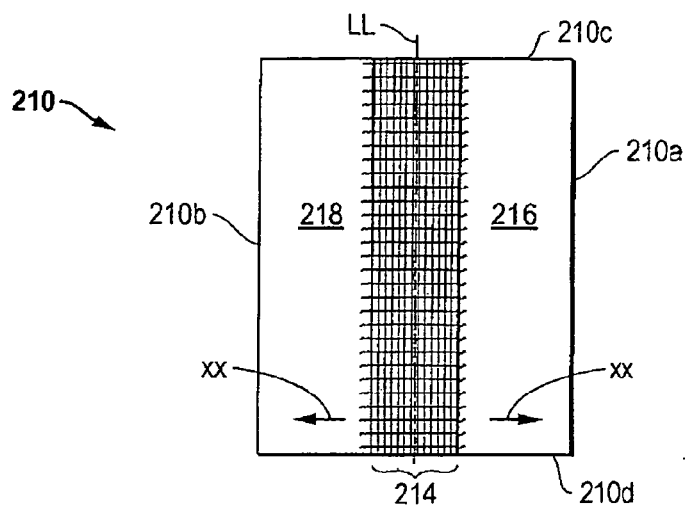
FIG. 2B is a plan view of the elastic composite of FIG. 2A shown in an extended, stretchable condition.
Figure 3:
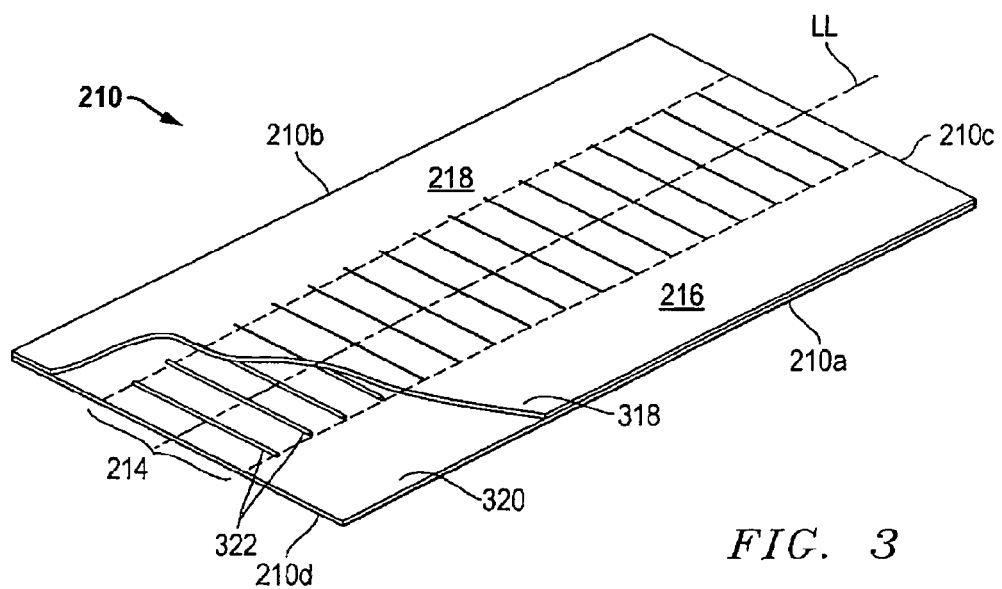
FIG. 3 is a perspective view of the elastic composite of FIG. 2A with a cut-out to show an elastic construction.
Figure 4:
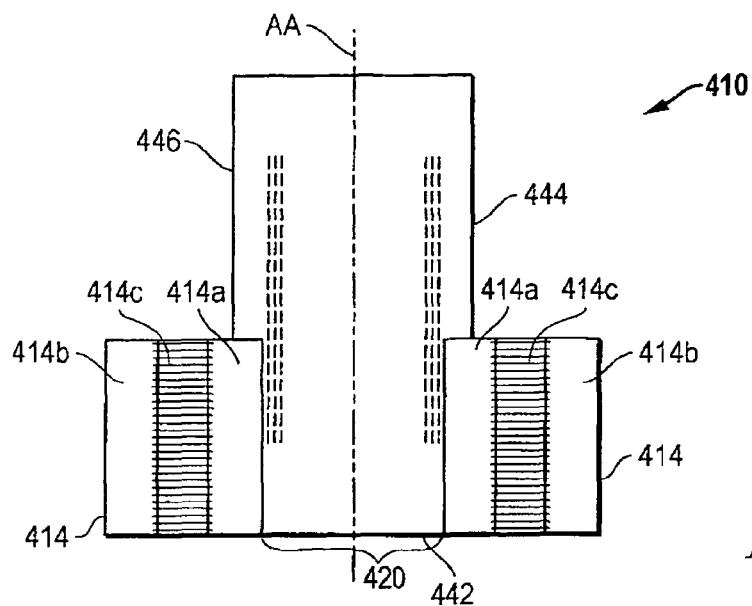
FIG. 4 is a plan view of another disposable absorbent garment.

FIGS. 1-11 are provided for background and to illustrate structures and processes potentially relevant to the present invention. Some Figures, and accompanying description, are provided to illustrate the prior art and for the purpose of highlighting the contributions to the prior art provided by the present invention. The same Figures also illustrate use of the elastic composite, system, or method of the invention, and/or a product derived from the inventive elastic composite. In particular, each of FIGS. 1 and 4 depicts a garment that incorporates an elastic composite structure or elastic composite as described and disclosed in the prior art. The elastic composite (having a single elasticized region) shown may, however, be provided by, or derived from, the elastic composite (having dual elasticized regions) of the present invention.

In FIGS. 1 and 4, a disposable absorbent garment is shown that is suitable for the invention and in the form of a diaper having one or more elastic composites incorporated therein. FIGS. 6-10 illustrate a system, system components, and a process of making the elastic composite having a single elasticized region as previously described and disclosed in the prior art. See U.S. Pat. Nos. 7,462,172 and 7,361,246. These Figures and accompanying descriptions of the prior art are provided to facilitate description of the present inventive elastic composite and highlight the differences and improvements provided by the present inventive system and method.

The described prior art systems and processes are particularly focused on the application or integration of the elastic elements upon or with one of the layers of the composite. In one aspect of the present invention, the invention is also focused on the application or integration of such elastic elements. In a further aspect of the present invention, the invention provides a process of integrating elastic sub- or pre-composite structures onto a base element such as a base non-woven web to generate an elastic composite having dual and independent elasticized regions.

The disposable absorbent garment 110 in FIG. 1 is of a type that can be placed against or in proximity to the body of a wearer so as to absorb and to contain various bodily exudates. It should be noted, however, that the present invention is applicable to a variety of disposable absorbent articles and garments, including training pants and a variety of adult incontinence products. As will be described below, the inventive elastic composite or elastic composite band may provide a side panel or ear portion, a waistband, a fastening tab or band, or other distinct elastic component of the garment or article. The inventive elastic composite may also be incorporated into an ear portion to elasticate the ear portion or to supplement the ear portion with an elasticated fastening tab.

FIG. 1 is introduced to illustrate some basic features of a disposable diaper 110. The diaper 110 includes three main regions aligned along an imaginary longitudinal axis or plane AA. These regions include a first waist region 112 (typically at the front of the user when the garment 110 is worn), a back waist region 114, and a crotch region 116. The diaper 110 is also characterized by a front edge 140, a back longitudinal edge 142, a first lateral or side edge or side margin 144, and a second lateral or side edge or side margin 146.

Along a lateral direction, the diaper 110 includes ear regions or ear portions 118 extending laterally from the waist regions 112, 114. Together, the waist regions 112, 114 and crotch region 116 may be referred to as forming a central body portion 120 of the garment 110 that is positioned within side edges 144, 146. The body portion 120 may also be referred to as being formed by a liquid permeable inner layer or topsheet 152, a liquid impermeable outer layer or backsheet (not shown), and an absorbent core 154 sandwiched between the two layers. The ear portions 118 further include fastening tabs 124 for attaching the waist regions 112, 114 together. The diaper 110 also has an elastic waistband 130 positioned generally along the back edge 142 to facilitate fastening and to enhance the fit and seal of the diaper 110. When the hourglass shaped diaper 110 is worn, the crotch region 116 fits about the crotch of the wearer, and the front and back waist regions, 112 and 114, fit about the corresponding waist areas. The ear portions 118, on the other hand, wrap about the wearer and the fastening tabs 124 engage to form a complete, all-around waistline of the diaper 110.

FIG. 2A depicts a typical elastic composite band 210, now generally known in the art, but which may also be derived from the elastic composite of the present invention. The elastic composite band 210 is one particularly suited for use as a side panel or fastening tab of a disposable absorbent garment (see, e.g., FIG. 1). FIG. 3 provides a perspective view and partial cutout of the elastic composite band 210. The elastic composite band 210 may be characterized by an imaginary centerline LL. The centerline LL preferably corresponds with the machine direction of the elastic composite band 210 during manufacture. The elastic band 210 also has side or longitudinally extending side edges 210a and 210b and laterally extending end edges 210c and 210d. In FIG. 1, the elastic composite band 210 is shown in the stretched state as, for example, when a garment incorporating the elastic composite band 210 is worn. In this state, the elastic composite band 210 stretches, in the lateral or cross-machine direction (denoted by arrows XX).

As used herein, the term "machine" direction refers to the direction at which the component, or more particularly, the material web from which the elastic composite is derived (e.g., cut from) is driven in an assembly line during manufacturing. The term "cross-machine direction" or "cross-directional," on the other hand, refers to the direction that is perpendicular to the machine direction. With reference to the elastic composite 210 of FIG. 2, the cross machine direction is the direction XX extending laterally or perpendicularly relative to the longitudinal line LL.

The elastic composite band 210 has a central region 214 in which an elastic construction is situated. Extending laterally from this central elastic or elasticized region 214 are regions 216 and 218, which are substantially non-elasticized ("dead zones"). As shown in FIG. 2A, the regions 216, 218 occupy the expanse between the central elastic region 214 and the side edges 210a, 210b. Now with reference to FIG. 3, the elastic composite band 210 has a top layer 318 and a bottom or base layer 320. The two layers 318, 320 preferably extend the total width and length of the elastic composite band 210, thereby providing the side edges 210a, 210b, and the end edges 210c, 210d. Both the base layer 320 and the top layer 318 are preferably a non-woven, breathable, disposable material such as propylene, non-woven fabric, breathable polyethylene/polypropylene films, or non-porous films (or combinations of these materials). The base layer 320 and top layer 318 adhere to one another, thereby sandwiching and securing a plurality of elastic strands 322 therebetween.

The elastic strands 322 may be substituted by suitable elastic elements such as elastic strands, threads, ribbons, and elastic glue beads. The elastic elements or strands 322 are distributed along a direction that extends between the side edges 210a, 210b and generally parallel with (or corresponding to) centerline LL. Further, each elastic element 322 is generally aligned or oriented in a direction corresponding with the lateral or cross-machine direction, i.e., in a direction generally perpendicular to the longitudinal center line LL and intersecting the side edges 210a, 210b. Preferably, the elastic elements 322 are disposed in generally parallel relation and spaced apart generally equally along the longitudinal direction. More preferably, the elastic elements 322 are of generally equal length. Accordingly, when the elastic composite band 210 is worn, the elastic elements 322 impart elasticity to the structure which allows the band 210 to stretch in the lateral or cross-machine direction XX. Because the elastic elements 322 are independent, spaced apart and maintained along the generally lateral direction, the stretch and contraction of the elasticized material are generally in the lateral direction as well. This alternative may be functionally and aesthetically advantageous in some garment applications.

The elastic elements 322 are preferably tensioned during securement between the top and base layers 318, 320. FIG. 2B illustrates the elastic composite band 210 in a laterally stretched condition. In this condition, the central elastic region 214 has a width that is almost equal to the non-elasticized zones 216 and 218. When returned to the non-laterally stretched or relaxed condition, as shown in FIG. 2A, the central elastic region 214 contracts and crimps to a substantially reduced width. In this condition or state, the contracted elastic elements 322 shirrs the elastic composite 210 and provide pleats 234 in the contracted elastic region 214.

In one application of the present invention, a reel or roll of a web of an elastic composite having dual elasticized regions is provided. The elastic composite is typically cut along the longitudinal centerline to produce two separate elastic composites. Such a reel or roll may be readily integrated into, and/or provide as input to a system and process for manufacturing a disposable absorbent garment. In one aspect, such a reel or roll is an output of a method of making an elastic composite according to the present invention.

Returning to FIG. 1, the disposable absorbent garment 110 employs one or more elastic composite bands, as described above. The disposable absorbent garment 110 employs in each of the ear portions 118, a fastening tab 124 having an elastic composite construction. As the fastening tab 124, the elastic composite band is configured such that one non-elasticized region 124a is attached to and overlaps the central body 120 of the garment 110 while a second non-elasticized region 124b is situated outboard of the side margins 144, 146. An elasticized region 124c, as shown in FIG. 1, provides elasticity, and thus, stretch in the lateral or cross-machine direction (of the elastic composite). In respect to the rest of the garment 110, the elasticity or stretch provided by the central elastic region 124c directed along a direction that is generally perpendicular to the longitudinal center line AA of the garment 110, and corresponds with a direction that wraps about the waistline of the user.

The disposable absorbent garment 110 in FIG. 1 also provides an elastic composite, as the waistband 130. The waistband 130 is situated centrally in the waist region 114. Further, the elastic composite waistband 130 is disposed such that non-elasticized regions 130a, 130b are positioned outwardly of the longitudinal line AA of the garment 110, while an elasticized region 130c is positioned centrally across the longitudinal center line AA. Moreover, the elasticized region 130c is configured such that the elastic strands are aligned or oriented in a direction that is generally perpendicular to the longitudinal centerline AA. In this way, the elastic composite waistband 130 imparts elasticity about the waist region 114 of the garment 110, and in a direction corresponding with the direction of waistline about the user.

FIG. 4 depicts an alternative disposable absorbent garment 410. Specifically, FIG. 4 depicts a disposable absorbent garment 410 employing elastic composites as attachable ear portions or side panels 414. The elastic composite side panels 414 are separate components that are attached to a central body 420 of the garment 410. The elastic composite side panels (or ear portions) 414 are attached near one waist edge 442 of the garment 410 and such that the centerline AA of the side panel 414 is generally parallel with the longitudinal centerline AA of the garment 410. Moreover, each of the elastic composite side panels 414 has a non-elasticized region 414a that is positioned outboard of the side margins 446 of the garment 410 and a second non-elasticized region 414b that is attached inboard of the side margin 446 (or side margin 444).

Figure 5:
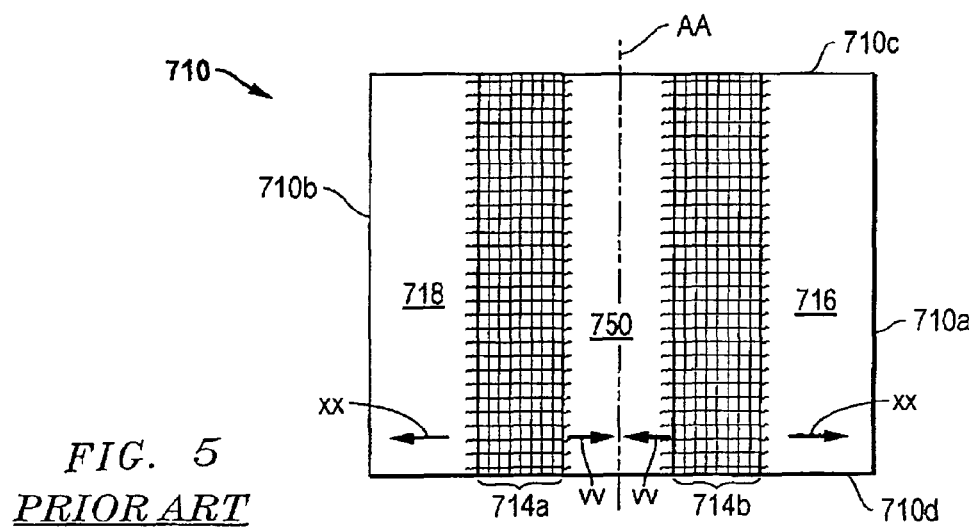
FIG. 5 is a plan view of an elastic composite having dual elasticized regions, according to the prior art.

FIG. 5 depicts an elastic composite 710 of the prior art that is different from the previously described elastic composite band (see e.g. FIG. 2) in that the elastic composite band 710 includes two elasticized regions 714a and 714b. The elasticized region 714a, 714b are preferably equidistantly spaced apart on either side of the longitudinal centerline AA. The spacing of the elasticized regions 714a, 714b creates right and left non-elasticized or dead regions 716, 718, as well as central non-elasticized region 750. The elasticized regions 714a, 714b imparts elasticity to elastic composite band 710a in the lateral directions XX, and in the central non-elasticized region 750, also in the opposite lateral direction VV. The elastic composite 710 may be employed as a dual elasticized component, or may be cut along the longitudinal centerline AA to produce two separate elastic composites each with a single elasticized region. Such elastic composite(s) may then be employed, for example, as any one of the elastic composites 124, 130, 410 in FIGS. 1 and 4. In one aspect of the present invention, an elastic composite having dual elasticized regions is provided as a direct improvement over the prior art elastic composite 710 shown in FIG. 5.

Before describing the elastic composite of the invention, FIGS. 6-10 are provided to illustrate a known system, and system components, and process of making or manufacturing an elastic composite, as previously practiced and described in more detail in U.S. Patent application Ser. Nos. 10/733,649 and 11/021,424. In the prior art process illustrated therein, two elastic composite web outputs 1031 are produced from four separate non-woven web inputs 1003a, 1003b, 1003c, and 1003d.

Figure 6:
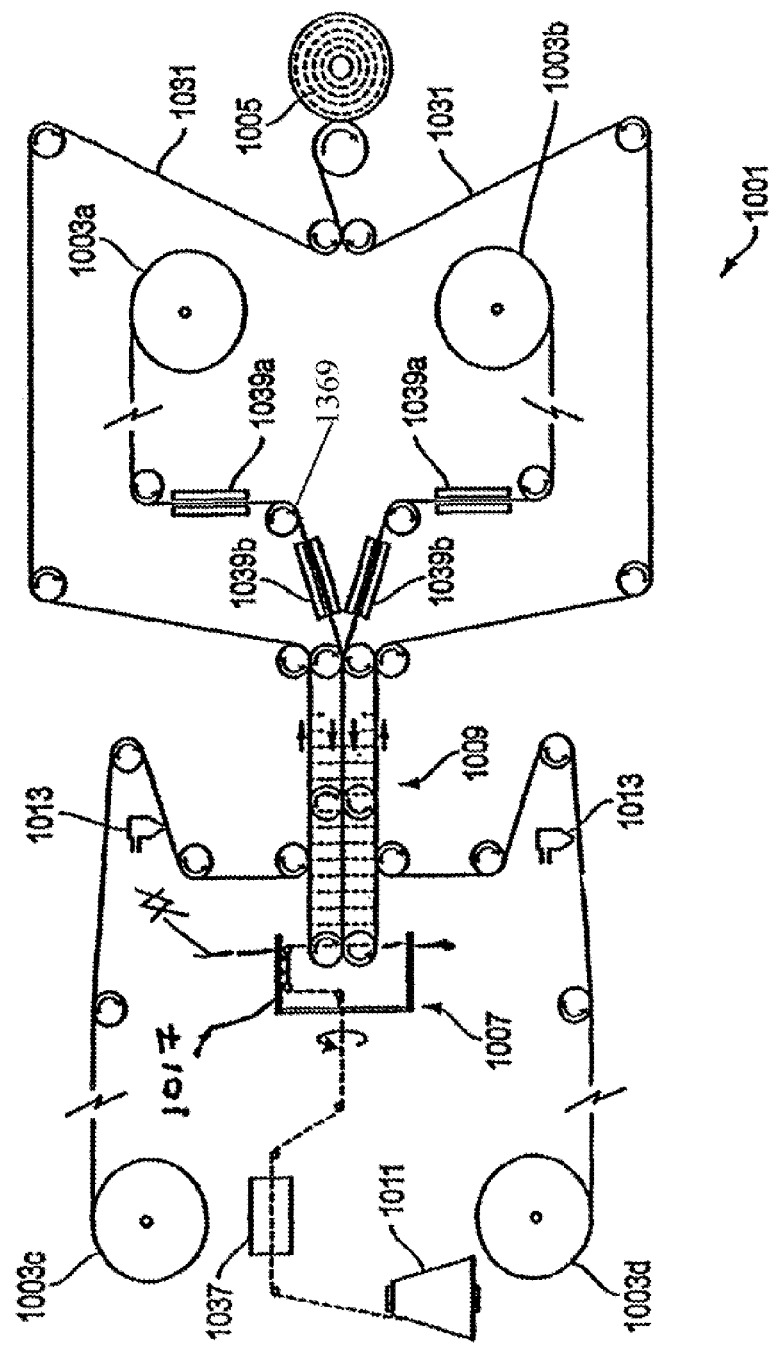
FIG. 6 is a simplified schematic of a system for manufacturing an elastic composite having a dual elasticized region, according to the prior art.

Referring first to FIG. 6, a system 1001 includes four separate non-woven web inputs 1003a-1003d, which provide a web or roll of non-woven material for the elastic composite. The system further includes an output assembly or reel 1005 that receives two elastic composite webs 1031 from the rest of the process. These two separate elastic webs may be later fixed together after manufacturing to produce the kind of composite (having two elasticized regions) described in respect to FIG. 5.

Central to the system 1001 is a conveyor assembly 1009 for receiving, manipulating, and conveying each of the non-woven web inputs. The conveyor assembly 1009 is positioned and operatively associated with an elastic element applicator such as a spinning head assembly 1007, that applies elastic fibers or strands upon, onto, and/or integrally with the non-woven web inputs. The spinning head assembly 1007 further includes a spinhead 1017, preferably in the form of a spinning bracket, or cylinder 1017 and the like. The spin cylinder 1017 is configured to hold an "end section" of the continuous strand WW (shown in FIG. 8) of elastic and move it about a generally vertical plane XX in a reciprocal or repetitive pattern (relative to the conveyor assembly 1009). This plane XX is defined by the area within the spinning perimeter of the cylinder 1017 and which is traced by the outer most bracket or eye 1017b securing the strand of elastic WW to the spin cylinder 1017. The paths of the spinhead 1017 and the section of elastic strand retained thereby are provided on the plane XX.

As shown in the schematic of FIG. 6, non-woven inputs 1003a and 1003b are fed, utilizing a series of rollers, into the conveyor assembly 1009. Before the two non-woven webs are fed into the conveyor assembly 1009, the webs are directed through the folding guides or plates 1039. The folding guides 1039 serve to effectively reduce the overall width of the non-woven web by folding the lateral or side edges along a pre-determined, longitudinally-extending side fold line YY. The first folding guide 1039a initiates the first 90° turn while the second folding guide 1039b initiates a second 90° turn. The roller 1369 disposed in between the guide 1039a and 1039b facilitates the folding process. The two folding guides 1039 and roller 1369 may be referred together as a folding guide assembly.

The conveyor assembly 1009 is set up so as to guide these two non-woven webs 1003a and 1003b through the center of the assembly 1009 towards and eventually inside the elastic spin cylinder 1017 (into the spinning path). Once inside the spin cylinder 1017 the conveyor assembly 1009 delivers the non-woven webs to each outside, upper and lower faces (outward faces) of the conveyor assembly 1009. At this point the direction of travel of the non-woven webs is reversed and the webs are directed out of the spin cylinder 1017. As the non-woven webs exit the spin cylinder 1017, an elastic strand WW is wrapped around the entire conveyor assembly 1009, and as it contacts the upper and lower face of the web platforms it comes into contact with the non-woven web. As shown in several of the Figures, the elastic strand WW is applied crosswise or laterally on the web, and transverse to the direction of the moving web. The friction between the tensioned elastic strand and the non-woven webs on the upper and lower faces of the conveyor assembly draws the "wrapped" elastic strand out of the spin cylinder 1017 and towards contact with two further non-woven webs 1003c and 1003d.

The non-woven webs 1003c and 1003d are operatively positioned upstream of an adhesive applicator 1013. Utilizing a system of rollers in conjunction therewith, the non-woven inputs 1003c, 1003d and adhesive applicators 1013 apply a web of pre-glued non-woven material onto the conveyor assembly 1009 and onto the elastic strand "wrapped" around the non-woven webs 1003a and 1003b.

Furthermore, the system 1001 employs a standard elastic input source, e.g., a bobbin of elastic yarn, that feeds elastic strands or fibers WW onto a tensioning/speed controlling unit 1037 and then to the spin cylinder or the spinning head 1017, so as to apply the strands WW onto the conveyor assembly 1009 and the non-woven material webs conveyed therethrough. Elastic is taken off the bobbin, box or positive drive system and fed through a tension and speed controlling motor towards the spin cylinder 1017. The elastic WW is delivered through a hollow shaft in the motor controlling the spin cylinder 1017. The elastic WW then passes into the spin cylinder 1017 and is guided by rollers, eyes or any other suitable mechanism around the inside face of the spin cylinder 1017.

Figure 7:
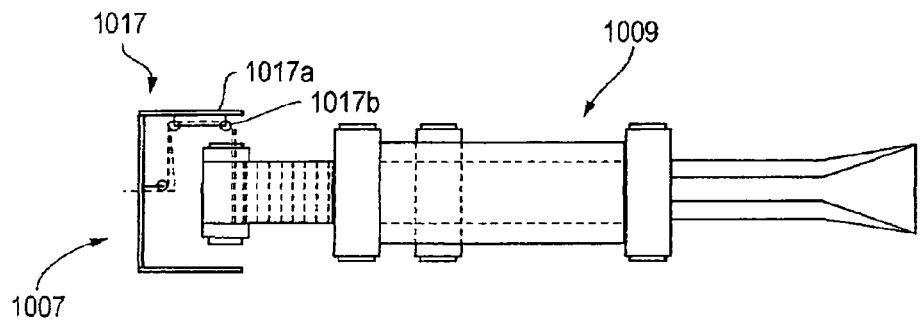
FIG. 7 is a top view of an elastic element applicator assembly for use with the system of FIG. 6.
Figure 8:
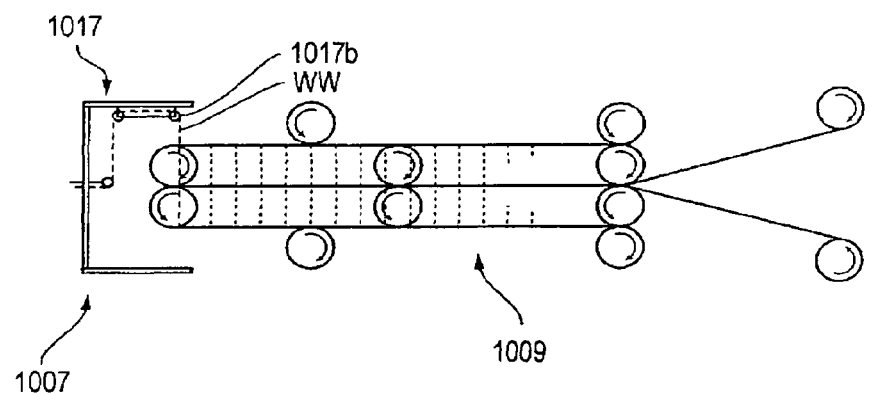
FIG. 8 is a side view of the assembly of FIG. 7.
Figure 9:
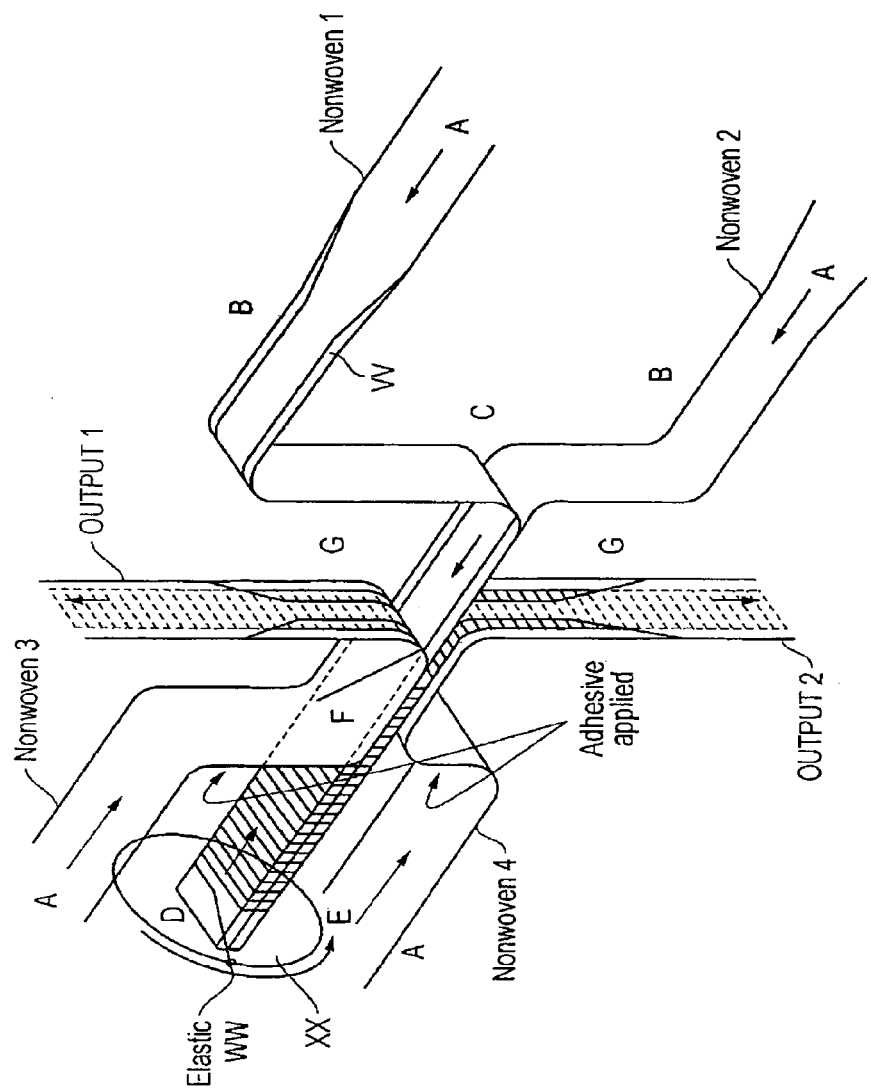
FIG. 9 is a simplified process illustration of making the elastic composite, according to the prior art.
Figure 10:
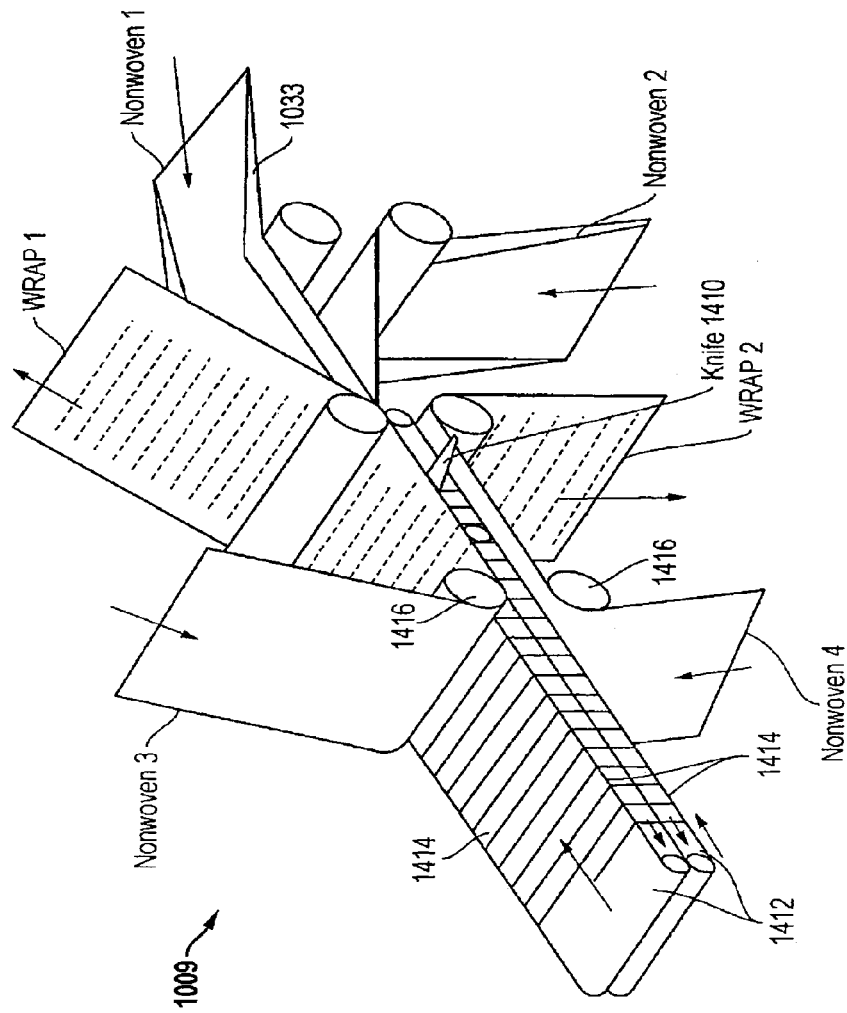
FIG. 10 is a detail view of a conveyor assembly for the system of FIG. 6.

FIGS. 7 and 8 provide alternate views of the spinning head assembly 1007 and conveyor assembly 1009. As discussed above, the conveyor assembly 1009 receives four separate webs of non-woven materials and outputs two webs 1031 of elastic composite. FIGS. 9 and 10 are provided to further illustrate the process of making the elastic composite. These figures, more particularly FIG. 9, illustrate the paths taken by the non-woven web materials to and from the conveyor assembly 1009.

Referring to FIG. 9, reference letters A-G are used to refer to stages in the process and in conjunction with the description of the process. As discussed above, non-woven raw material webs are fed into the process at stage A. These webs provide four separate non-woven web inputs into the process. Non-woven webs 1 and 3 are combined to make an elastic composite output 1 (i.e., referred to in the Figures as the WRAP output). Non-wovens 2 and 4, which are both on the downside of the spinning head assembly 1007 and conveyor assembly 1009, combine to make a second elastic composite output 2 (i.e., WRAP 2).

At stage B, non-woven webs 1 and 2 are folded prior to being directed to the conveyor assembly 1009. A predetermined width of non-woven is folded over each side of the web to make two folded flaps VV. The width of the flap VV determines the width of the dead zone or non-elasticized region described previously, while the width of the non-woven, after folding, determines the width of the elasticized region. At stage C, the non-woven webs 1 and 2 are fed into the conveyor assembly 1009, in particular into the middle or inside of the conveyor assembly 1009 with the folded side of each web facing the outside of or away from the conveyor assembly 1009. It should be noted that at this stage C, non-woven webs 1 and 2 are not bonded together. The conveyor 1009 then feeds the non-woven webs 1 and 2 towards the spinning head assembly 1007. At stage D, the non-woven webs 1 and 2 have traveled almost the length of the conveyor assembly 1009 and progresses into the spinning path of spinning head assembly 1007 and intersecting the "spinning" vertical plane XX of the elastic strand WW. Further, at the end of the conveyor assembly 1009, the webs 1 and 2 are directed away from each other and onto the outside of the conveyor 1009 and away from the spinning head 1007. Non-woven web 1 turns up on the upper side of the conveyor assembly 1009, while non-woven web 2 travels along the lower side of the conveyor assembly 1009. At stage E, an elastic strand WW is wound around the folded non-woven webs 1 and 2, as these webs pass through the spinning head and the vertical plane XX. The elastic strand WW is applied to the moving webs 1 and 2 cross-directionally to the direction of the moving web. The movements of the webs 1 and 2 away from within the spin cylinder 1017 draws the "wrapped" elastic strand out of the spin cylinder 1017.

Figure 16:
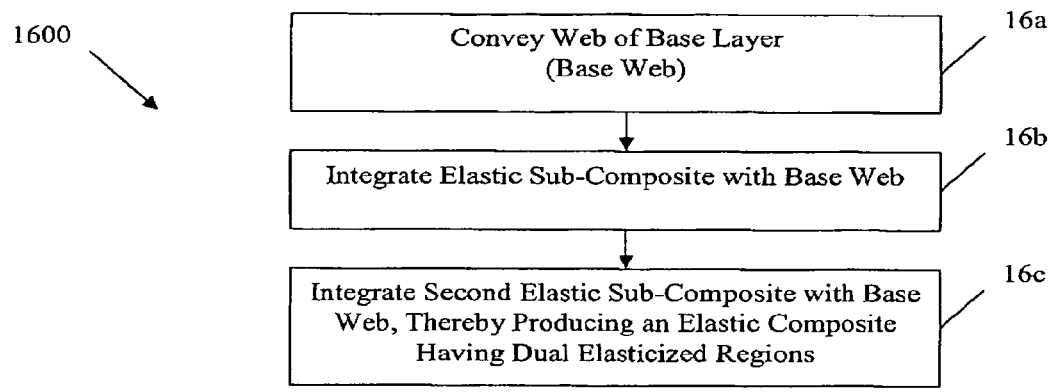
FIG. 16 is a simplified flow chart illustrating basic steps or stages of a method of making an elastic composite having dual elasticized regions, according to the present invention.

Now turning to non-woven webs 3 and 4, these webs are provided to the conveyor assembly 1009 with adhesive applied on one side (i.e., applied by the adhesive applicator 1013). At stage F, the non-woven webs 3 and 4 are brought into contact with webs 1 and 2, respectively, and the elastic strands WW. As a result, the webs 1 and 3 sandwich elastic strands WW on the upper side of the conveyor assembly 1009, and non-woven webs 2 and 4 sandwich elastic strands WW on the under side of the conveyor assembly 1009. The elastic strands WW run between the two non-woven elastic non-woven composite (cross-direction), but is then cut by a knife (see knife 1410 in FIG. 10, as described below), thereby separating the two wrapped composites. At stage G, the composites 1 and 2 are fed away from the conveyor assembly 1009 and the folded flaps on webs 1 and 2 become unfolded, with guiding, to form a flat non-woven composite. Subsequently, the composites are guided from the spinning head assembly 1007 and conveyor assembly 1009 and into further processes. As shown in FIG. 16, the elastic output webs arrive via a system of rollers onto an elastic composite output reel 1005.

FIG. 10 provides an alternate view of the conveyor assembly 1009. This Figure further illustrates the movement of non-woven webs 1-4, and the application of elastic strands in a generally mutually parallel pattern and generally spaced apart from one another. After cutting of the elastic with the knife 1410, two elastic composites are directed away from the conveyor assembly 1009. It should also be noted that the system advantageously allows for improved control of the stretch of the elastic strands.

As shown in FIGS. 8 and 10, the conveyor assembly 1009 preferably includes two web moving platforms 1412 which are juxtapositioned so as to provide an interface therebetween. Each web moving platform 1412 includes a continuous belt 1414 supported about a plurality of rollers 1416 so as to be capable of reciprocal motion. The two web moving platforms 1412 are generally the same length and juxtapositioned so as to accommodate the non-woven webs 1 and 2 therealong from one end to the other end. Preferably, a roller 1416 is situated about midway between the ends of the web moving platform so as to deliver the non-woven webs 3 and 4 respectively to the web moving platform.

As shown in FIG. 6 and also FIG. 10, the spinning head assembly 1007 is positioned about and in the vicinity of one end of the conveyor assembly 1009. In operation, the spinning head 1017 spins about the vertical plane XX which intersects the ends of the web moving platforms 1412 so as to deliver the elastic strands WW around and about both web moving platforms 1412. In operation, the first and second non-woven move along the outside or exposed surfaces or sides of the web moving platforms 1412 and receives the elastic strands WW delivered by the spinning head 1017. By way of its movement away from the spinning head 1017, the moving web draws the continuous elastic strand WW from the spinning head 1017.

By pre-folding the two non-woven webs that are fed to the inside of the conveyor assembly 1009, it is possible to create an elastic composite with cross directional stretch having non-elasticized regions ("dead zones") along each edge. The width of the central elasticized region is fixed to the width of the conveyor platform 1412. The width of the non-elasticized regions or dead zones is determined by the width of the fold VV. The fold VV in the non-woven is preserved by the conveyor assembly 1009 during application of the elastic element and is applied in such a way that the folded edge of the non-woven is not in contact with the elastic element WW. The fold VV is then allowed to open after the composite exits the conveyor assembly 1009 to provide a flat elastic composite with non-elasticized regions. By altering the alignment of the materials as it enters the conveyor assembly 1009 or by changing the widths of the materials used it is possible to create various composite designs.

FIGS. 6-10 and the above accompanying description illustrate a method of making an elastic composite that is different from and precedes the present invention. Most of the steps, sub-processes, components and sub-systems can be employed, however, in the systems and methods of the present invention (which are described later in reference to FIGS. 17-21). In fact, applicable detail descriptions of system components and operation may be borrowed from this portion of the specification in explaining the inventive systems, and methods later in this disclosure. Differences between the previously disclosed systems and the systems to be described, in respect to the present invention, represent, or arise from, improvements provided by the present invention. Such differences are discussed herein in more detail.

The above-described process provides an elastic composite with cross directional stretch properties and a single elasticized region. The process also provides non-elasticized regions on either side of the central elasticized zone of the composite. The focus of the remaining descriptions shifts now to an elastic composite having dual elasticized regions.

Figure 11A:
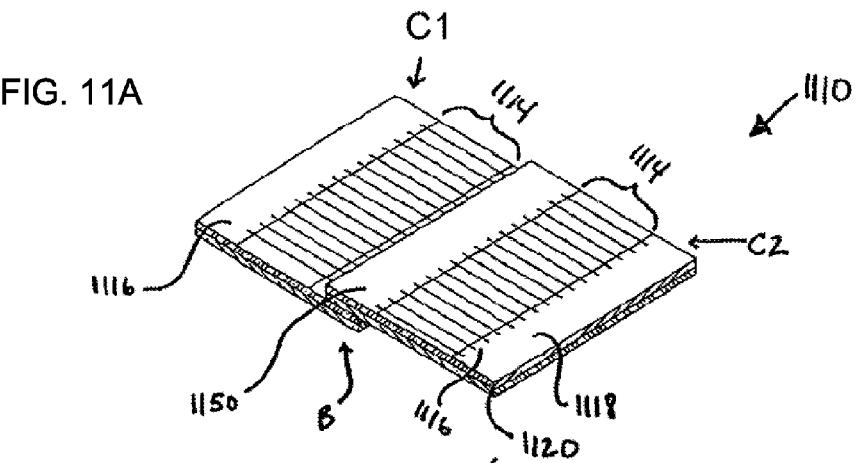
FIG. 11A is a perspective view of an elastic composite having dual elasticized regions.
Figure 11B:
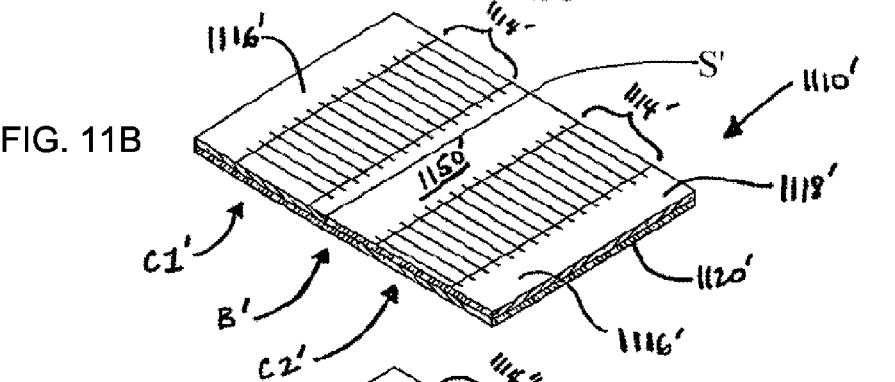
FIG. 11B is a perspective view of another elastic composite having dual elasticized regions.
Figure 11C:
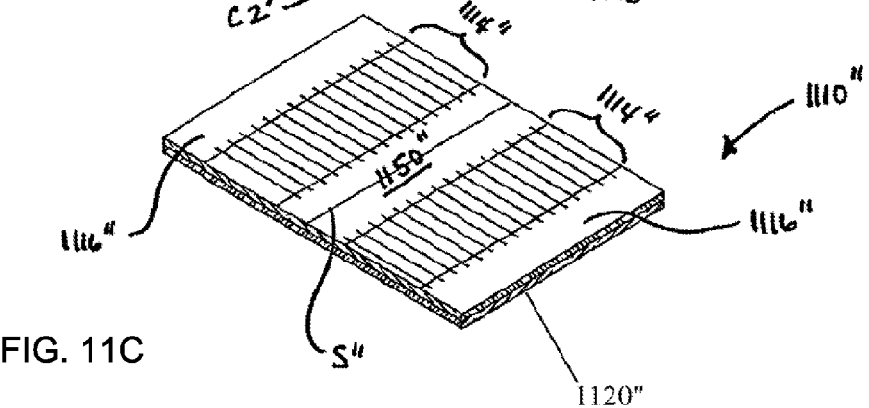
FIG. 11C is a perspective view of yet another elastic composite having dual elasticized regions.

Each of FIGS. 11A-11C illustrates an elastic composite 1110 containing a pair of elasticized regions 1114. The elastic composite 1110 also has three non-elasticized zones or dead zones, including a central dead zone 1150 extending longitudinally between the two elasticized regions 1114 and side dead zones 1116 positioned on the other side of each elasticized region 1150. The elastic composite 1110 may now be referred to herein as an elastic composite having dual elasticized regions. Such an elastic composite may also be referred to as a dual elasticized elastic composite.

In FIG. 11A, the elastic composite 1110 shown is formed from two discrete composite sections C1, C2. Each composite section C1, C2 is manufactured independently as a discrete elastic composite having a single elasticized region, employing, for example, the system described above in respect to FIGS. 6-10. Each elasticized region is "independent" of the other elasticized region in that each was applied and integrated with a top and/or base layer in a construction different from that of the other elasticized regions. To form the dual-elasticized elastic composite, two of the singly elasticized composite sections C1, C2 are joined together by overlapping one side edge of one composite section over a side edge of the other composite section. A suitable adhesive or adhesive means may be used to maintain bonding at the overlap. The overlap creates a multi-layer bonding portion B as shown in FIG. 11A, which also serves as a portion of the central dead zone.

The bonding portion B consists of a top non-woven layer 1118 and a base layer 1120 of each composite section. Accordingly, the thickness of the bonding portion B and the central dead zone 1150 may be, at least observably, greater than the thickness of the rest of dual-elasticized elastic composite. For each composite section C1, C2, the top non-woven layer 1118 and the base non-woven layer 1120 have the same width and the side edges are aligned. In further descriptions, reference to the side edge of base layer may apply to the "side edge" of the elastic composite, and vice-versa.

Turning to FIG. 11B, a second dual-elasticized elastic composite 1110' is shown again consisting of two adjoined singly elasticized, composite sections C1', C2'. For each composite section C1', C2', one of a top layer 1118' and a bottom layer 1120' is wider than the other. Referring to the view of FIG. 11B, the right composite section C2' has a bottom layer 1120' that extends farther laterally than the top layer 1118', thereby forming a step. For the left composite section C1', the top layer 1118' extends farther laterally than the bottom layer 1120', thereby forming a ledge. By abutting the ledged side edge to the stepped side edge, a suitable construction joint is provided between the two composite sections C1', C2'. An overlapping bonding portion B' (and central dead zone 1150') is also provided that consists of a single top layer 1118' and a single base layer 1120' and is characterized by a thickness generally consistent with the other portions of the dual elasticized elastic composite 1110'. A suitable adhesive or adhesive means may be employed to facilitate and maintain bonding between the layers of the bonding portion.

FIG. 11C illustrates an improved dual elasticized elastic composite 1110". In addition to a pair of elasticized regions 1114", the elastic composite also has two side dead zones 1116" and a central dead zone 1150" situated between the elasticized regions 1114". The thickness of the dead zone 1150" is provided by a single top layer 1118" and a single base layer 1120" and is, therefore, consistent with the thickness of other portions of the dual elasticized elastic composite 1110". The dual elasticized elastic composite 1110" provides a single composite structure. The base layer 1120" of the elastic composite 1110" is provided by a seamless sheet of non-woven (or other material). The elastic composite 1110" does not require joining of two discrete elastic composite sections. Rather, a web of the dual elasticized elastic composite 1110" is generated linearly as output of the manufacturing process. As a seamless composite structure, the dual elasticized composite 1110" eliminates the bonding region required of the elastic composites in FIGS. 11A and 11B and thus, avoids the potential for leakage generally associated with these bonding regions B, B'. The seamless composite structure is also more structurally sound than the other composites and has a higher tensile strength (laterally and longitudinally).

As used herein, the term "seamless composite structure" shall refer to a structure that does not have a seam at which two or more originally independent sections are joined as one to form the present structure. It should be noted that the top layer 1118" of the elastic composite 1110" in FIG. 11C may provide a single seam S" along the central dead zone 1150" and thus, may not be referred to as "seamless." This seam S" of the top layers 1118" is not, however, a seam of the elastic composite 1110" as that seam S" does not extend through the thickness of the dead zone 1150" and the multi-layer composite 1110", and is not required to join two independent sections of the elastic composite 1110".

As expected, the dual elasticized elastic composite 1110" is generally easier to manufacture than the other composites in that it does not require the joining and bonding steps required described previously. It also does not require the machines or manpower to implement these steps. Furthermore, the seamlessness of the elastic composite 1110" is generally more aesthetically pleasing than the bonding regions B, B'. By eliminating or reducing the use of adhesives, the central dead zone of the elastic composite 1110" is also generally cleaner.

In each of the elastic composites 1110' and 1110" (FIGS. 11B and 11C), the top layer extends over and past the elastic elements to the side edge or inwardly to the bonding seams S' and S". In each of the elastic composites 1110' and 1110" of FIGS. 11B and 11C, respectively, the central dead zone (1150', 1150") is composed of a top layer having a seam (S', S") and a base layer. Similarly, the side dead zones 1116', 1116" are also constructed of at least two non-woven layers. To maintain a neat and uniform construction in these dead zones 1116', 1116", the top layer and base layer are attached together using adhesives. As will be further explained below, these adhesive areas are susceptible to failure due to excessive or repeated loading, moisture, or deficient adhesive application. The application of adhesives can also be messy and unsightly.

For purposes of the present description, the term "non-woven" is used to describe the principal material used in the construction of the material layers of the elastic composite. However, it should be noted that this invention is not limited to non-woven materials but may be applied to any material that is available in the form of a continuous sheet. Other materials suitable for this application include PE film, PE film/non-woven laminates and tissue.

Figure 12:
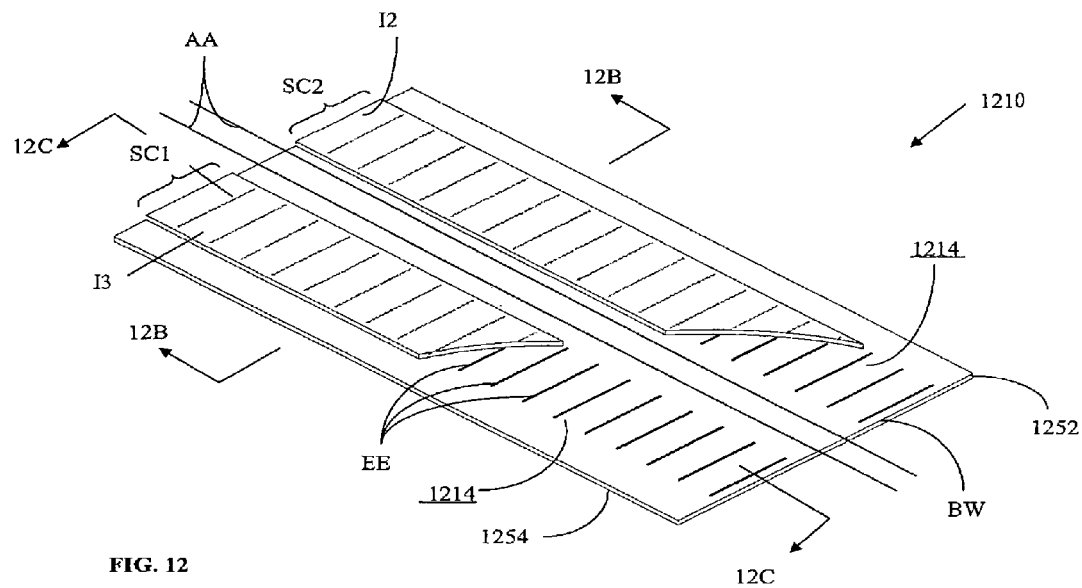
FIG. 12 is a simplified perspective view, including a cutout, of an elastic composite having dual elasticized regions, according to the present invention.

FIG. 12 illustrates an improved elastic composite 1210 having dual elasticized regions 1214, according to the present invention. The elastic composite 1210 may be characterized as having three primary components: a base layer BW, a first elastic sub-composite SC1, and a second elastic sub-composite SC2 spaced laterally from the first elastic sub-composite SC1. The first and second elastic sub-composites SC1, SC2 correspond to the dual elasticized regions 1214 of the elastic composite 1210. The base layer BW is preferably a non-woven material having a first lateral side edge 1252 and a second lateral side edge 1254, which, in many applications, will provide a generally straight longitudinally extending line. The side edge(s) 1252, 1254 of the base layer BW also functions as the side edge(s) 1252, 1254 of the elastic composite 1210 in the embodiments described herein. Moreover, the base layer BW and the elastic composite 1210 may be described as having a longitudinally extending centerline AA that is consistent with a machine direction. The direction perpendicular to the centerline AA may be referred to as the lateral direction.

Figure 12A:
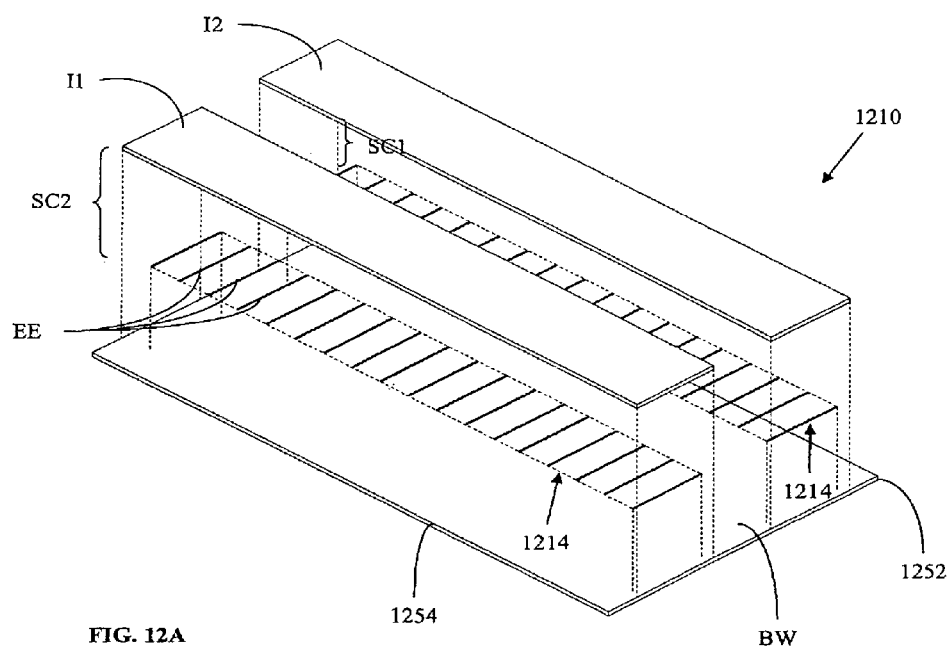
FIG. 12A is an exploded view of the elastic composite in FIG. 12.
Figure 12B:
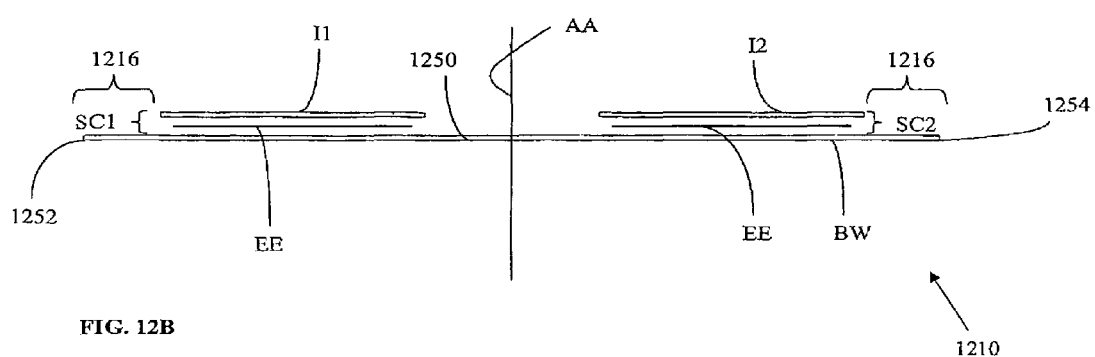
FIG. 12B is a lateral cross-sectional view of the elastic composite in FIG. 12, across line 12B-12B.
Figure 12C:
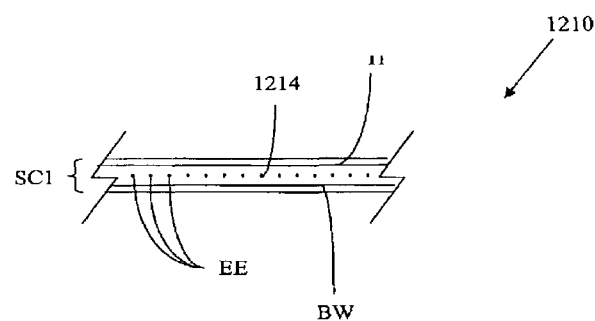
FIG. 12C is a longitudinal cross-sectional view of the elastic composite in FIG. 12, across line 12C-12C.

Each elastic sub-composite SC1, SC2, as further illustrated in the exploded view of FIG. 12A and the sectional views of FIGS. 12B and 12C, is preferably composed of a top nonwoven layer I1, I2 and an elastic construction 1214 over which the top layer I1, I2 extends. Further, the elastic construction 1214 is provided by a plurality of elastic elements EE that are mutually spaced apart and disposed in generally parallel relation. As shown in FIG. 12, the elastic elements are independent from one another, but within the same elastic construction, the elastic elements are preferably derived from the same continuous elastic strand. That is, the elastic elements have generally the same physical properties and are, in fact, severed sections of the same, previously continuous elastic strand. Each elastic element is directed along a lateral or cross-machine direction generally perpendicular to the longitudinal centerline AA. The elastic construction 1214 may be further described as providing a distribution of elastic elements that extend in the longitudinal or machine direction (and preferably in parallel with the longitudinal centerline). As further discussed herein, the elastic elements EE are preferably adhered to, first, the top layer by glue or equivalent, and secondly, in a similar fashion, to the base web.

As shown best in FIG. 12B, each elastic element EE extends laterally, but stops short of and is spaced apart from the side edge 1252, 1254. In one aspect of the present invention, the top layer I1, I2 of the sub-composites SC1, SC2 extends over the elastic construction 1214, but only slightly past the lateral extent of the elastic elements EE. Thus, as shown in FIGS. 12 and 12B, each elastic sub-composite SC1, SC2 is spaced laterally inward of the side edge 1252, 1254, to create a side non-elasticized region or dead zone 1216, 1218, the significance of which has been previously described. In this embodiment, the side dead zones 1216 are of a single layer provided by the base web BW.

The two elastic sub-composites SC1, SC2 are also mutually spaced apart to define the central non-elasticized region or dead zone 1250. As further illustrated in the cross-sectional view of FIG. 12B, the central non-elasticized region 1250, at least in this embodiment, consists of a single layer of the base layer BW. Further, the central non-elasticized region 1250 is seamless and requires no joining or constructing of materials, whether to join two halves of an elastic composite or adhere one layer to another layer. Accordingly, the elastic composite 1210 of the present invention is a seamless construction with a central dead zone 1250 that generally has a greater tensile strength than prior art constructions. The design of the elastic composite 1210 also eliminates any seams, which may be susceptible to failure and thus represent weak structural points.

It also follows that the elastic composite, according to the present invention, requires less material than prior art elastic composites having dual elasticized regions, which can translate to cost savings. Also, by eliminating the top layer in this region, the non-elasticized region can provide a more suitable and more reliable landing for a hook material. Furthermore, the single layer, seamless non-elasticized central region 1250 (and overall, the elastic composite) may be more aesthetically pleasing.

The elastic composite 1210 may appear, or be used in, a finished product (e.g., a disposable absorbent garment) as a component having dual elasticized regions. That is, the elastic composite may be used in the dual elasticized form shown in FIG. 12. It is also possible, however, that the elastic composites 1210 may be provided only temporarily in the dual elasticized form. Such may be preferred for storage, packaging and shipping, and/or marketing purposes. The dual elasticized elastic composite may, in further applications, be split and thus, converted to a pair of separate, singly elasticized elastic composites.

Figure 13:
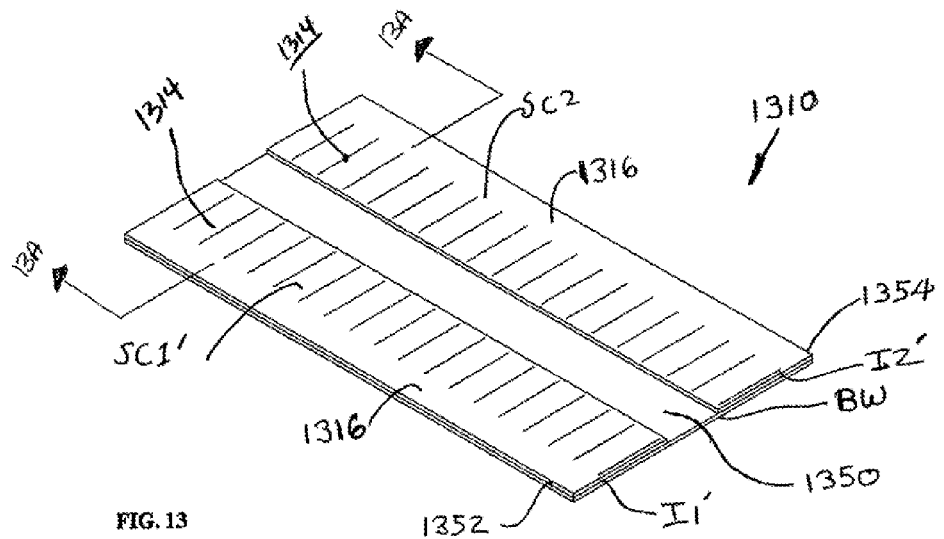
FIG. 13 is a simplified perspective view of an elastic composite according to an alternative embodiment of the present invention.
Figure 13A:
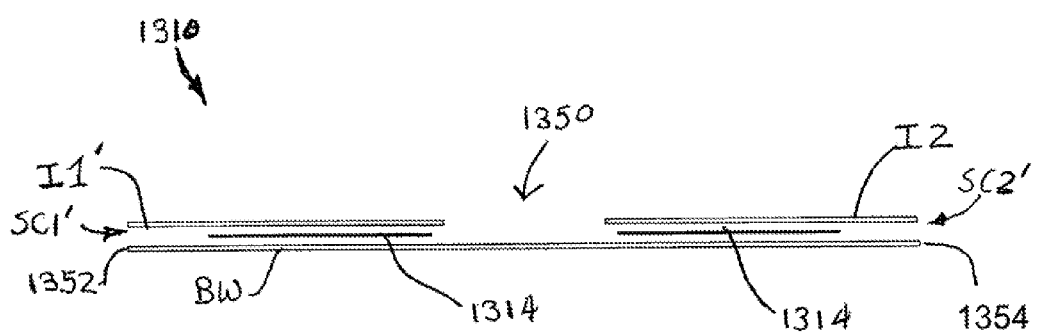
FIG. 13A is a lateral cross-sectional view of the elastic composite in FIG. 13.

FIGS. 13 and 13A depict an alternative embodiment of the elastic composite, according to the present invention. The alternative elastic composite 1310 is also provided with a base layer BW and dual elasticized regions 1314. The elasticized regions 1314 are laterally spaced apart to create a central dead zone 1350. Furthermore, the elastic elements of the elasticized regions 1314 are spaced inwardly of side edges 1352, 1354, thereby creating a pair of side dead zones 1316.

In this particular embodiment, a pair of elastic sub-composite SC1, SC2 are positioned on the base web BW along the side edges 1352, 1354. Unlike the elastic sub-composites SC1, SC2 in FIG. 12, the elastic sub-composite SC1', SC2', in this embodiment, extend to the side edges 1352, 1354. Thus, the dead zones 1316 of this elastic composite 1310 has a pair of double layer, side dead zones 1316.

Figure 14:
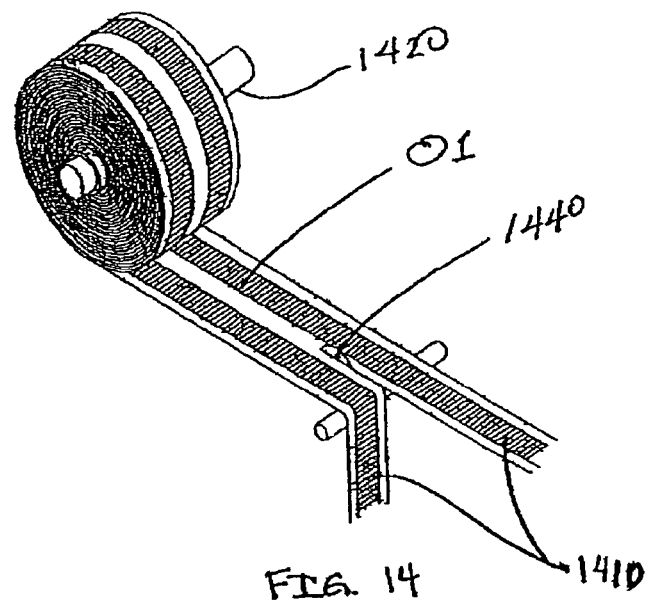
FIG. 14 is a simplified illustration of a roll or reel supporting a web of the elastic composite in FIG. 12.

FIG. 14 illustrates a roll or web O1 of an elastic composite 1210 having dual elasticized regions, according to the present invention. Such a roll or web represents the output of a process of manufacturing the elastic composite. In a suitable application, the elastic composite 1210 is preferably cut along the longitudinal centerline AA to produce two separate elastic composites, for use as described previously and as depicted in FIG. 1 for example (items 124 and 130). In the illustration of FIG. 14, the web O1 of the elastic composite 1210 is provided on a spool 1420 and then, delivered to a knife mechanism 1440 or other cutting means, located downstream of the spool 1420. Downstream of the knife mechanism 1440, two strips or webs 1410 of single elasticized elastic composites may be directed and/or fed to various stages of a system of manufacturing a disposable absorbent garment.

Figure 14A:
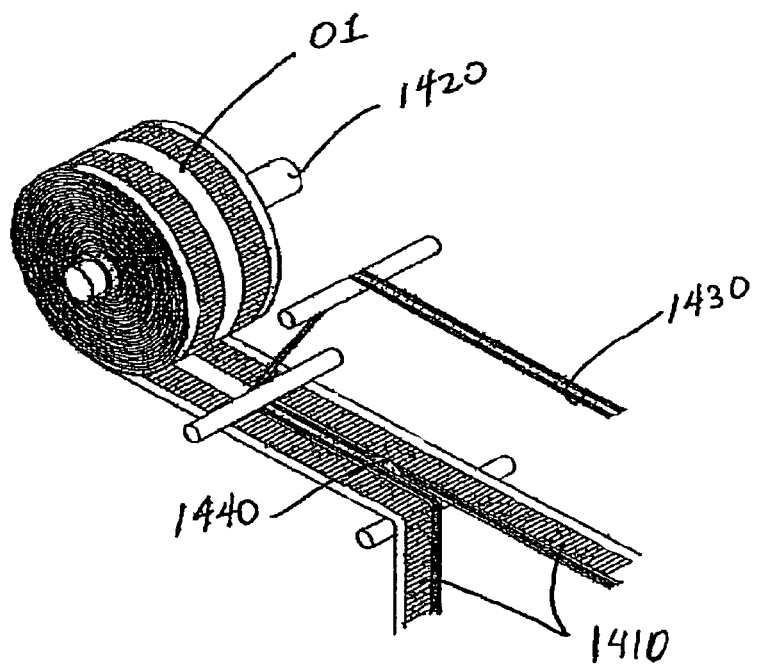
FIG. 14A is a perspective view of a roll or reel supporting a web of the elastic composite in FIG. 12, with hook material being applied thereto.

Referring now to FIG. 14A, a roll or web of the elastic composite is also shown being delivered from a spool 1420. In this illustration, two parallel strips 1430 of a hook material are delivered and applied to the moving web O1 of the elastic composite 1210 downstream of the spool 1420. The strips 1430 of hook material is preferably applied by glue on either side of the longitudinal centerline AA. The resulting web is then moved through the mechanism 1440 and cut along the longitudinal centerline AA. As a result, two webs 1410 of an elastic composite 1210 having a single elasticized region may be delivered and/or fed to various stages of a manufacturing process, ultimately providing an elastic composite and a disposable absorbent garment, as an ear panel, waist band, and the like. In further applications, a single strip of hook material may be applied to the web O1 and/or a shaped die cut may be employed instead of the longitudinal cut.

Figure 15:
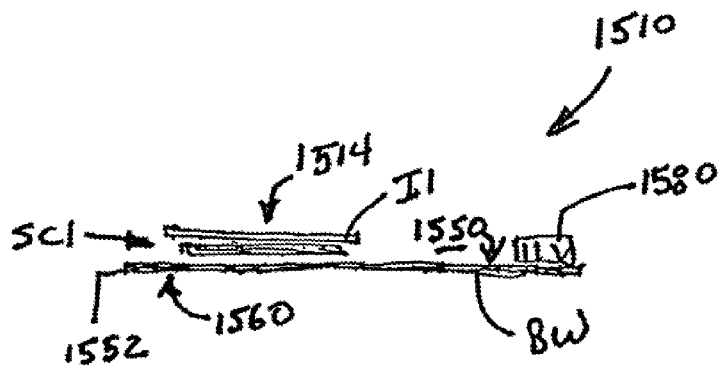
FIG. 15 is a lateral cross-sectional view of an elastic composite having a hook material applied thereon, according to the present invention.

FIG. 15 is a simplified illustration of an elastic composite strip 1510 derived from the web of elastic composite O1, as shown in FIG. 14A. The elastic composite 1510 represents one of the two elastic composites having a single elasticized region 1514 that may be cut from the longitudinally extending web 1410. The elastic composite 1510 has a base layer BW and an elastic sub-composite SC1 of an elastic construction and a top non-woven layer 11. The sub-composite SC1 provides the single elasticized region 1514. The elastic composite 1510 retains one-half of the previous central non-elasticized region 1550 (in contrast to the "full" central non-elasticized region in the web O1 of FIGS. 14 and 14A). The elastic composite 1510 also retains a side non-elasticized region 1560 between the elasticized region 1514 and a side edge 1552.

As shown in FIG. 15, the central non-elasticized region 1550 is composed of a single layer of the base web material BW. A hook material 1580 (or other fastening mechanism) is directly planted on the base layer BW in this non-elasticized region 1550, using adhesive means or the like. Loading on the hook material 1580 transfers directly to the base layer BW.

Figure 15A:
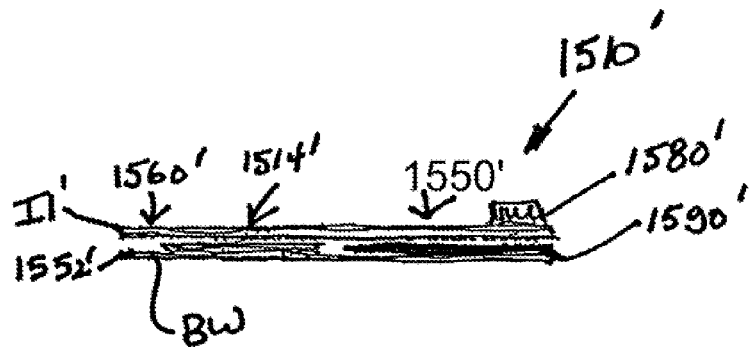
FIG. 15A is a lateral cross-sectional view of an elastic composite having a hook material applied thereon, according to the prior art.

FIG. 15A illustrates a prior art elastic composite 1510' with a single elasticized region 1514', a side non-elasticized region 1560', and a central non-elasticized region 1550'. The central non-elasticized region 1550' is provided by the base layer BW and the top layer I1' which extends laterally from the elasticized region 1514'. Unlike the elastic composite 1510 according to the present invention, a hook material 1580' (or other fastening mechanism) is glued directly to the top layer I1' in the central non-elasticized region 1550'. The top layer I1' is further glued to the base layer BW', also by known adhesive means 1590'. Thus, when the elastic composite 1510' is manipulated or the hook material 1580' is loaded, the adhesive 1590' between the top layer I1' and the base layer BW' must resist. If the adhesive 1590' is inadequate, the top layer I1' may be peeled off when the hook material 1580' is being pulled, for example. As one benefit of the elastic composite 1210 of the present invention, this potential weak spot is eliminated, thereby providing an elastic composite construction having greater structural integrity. Furthermore, elimination of the excess top layer and adhesive in the landing zone of the hook material may provide some reduction in material and construction costs. It may also result in a more aesthetically pleasing surface. Among other things, it is easier to prevent wrinkles or undulations in the landing area with a single layer material construction.

The simplified flow chart 1600 of FIG. 16 illustrates a set of basic steps or stages in a method of making an elastic composite having dual elasticized regions, according to the present invention. The simplified flowcharts of FIGS. 17 (1700) and 18 (1800) provide further exemplary variations of the inventive method. The simplified system illustrations of FIGS. 19 and 20 each provide an exemplary system that may be employed to produce the inventive elastic composite. More specifically, the system of FIGS. 19 and 20 may be employed to generate a continuous web or roll O1 of an elastic composite 1210 having dual elasticized regions, according to the present invention.

Turning first to FIG. 16, the inventive method generally begins with the provision of a web of a base material or base layer. As discussed previously, in these preferred embodiments, the base layer is provided by a non-woven material. Generally, in an initial step 16a of the inventive method, a web of the base layer is conveyed, preferably toward a central integrating assembly of the manufacturing system. Then, an elasticized sub-composite is integrated with the base web (Step 16b). As discussed in respect to the exemplary embodiments of FIGS. 12 and 13, the elastic sub-composite may be a construction consisting of a top non-woven layer and a plurality of elastic elements that are spaced apart and disposed in generally parallel relation. Further, in a subsequent step 16c, a second elastic sub-composite is integrated with the base web, which preferably already has the first elastic sub-composite integrated. In this manner, an elastic composite having dual elasticized regions is produced, according to the present invention.

Figure 17:
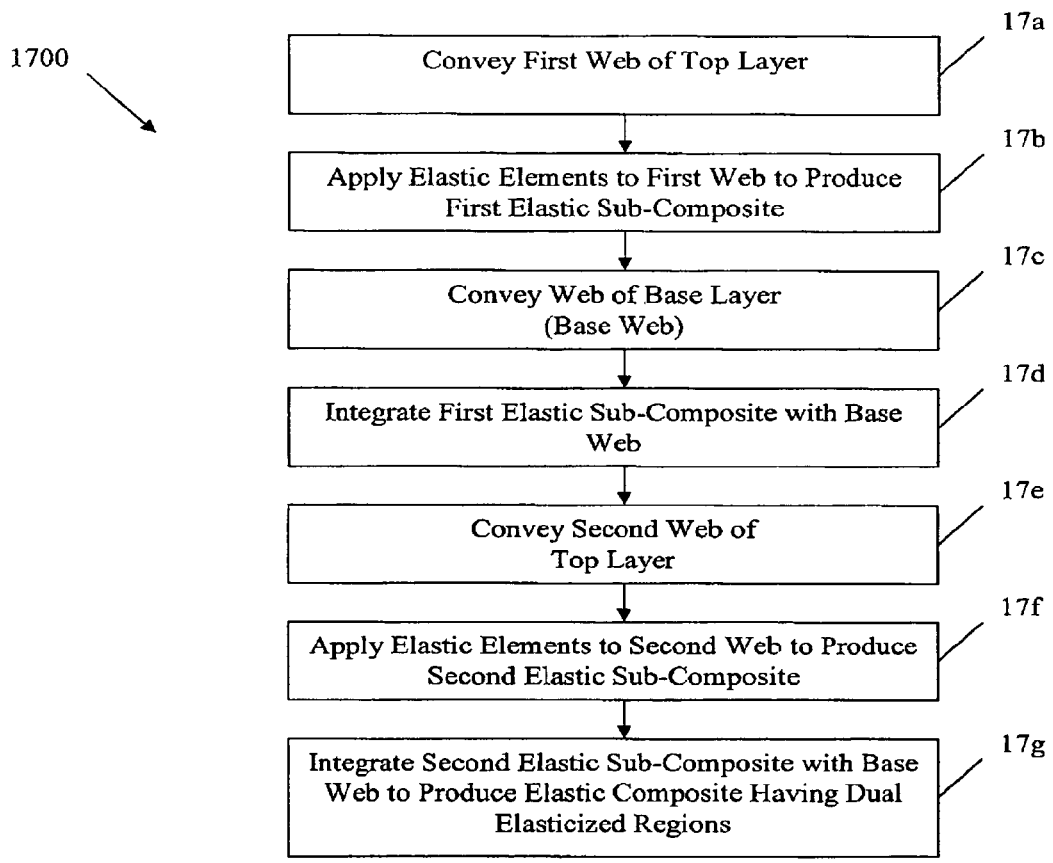
FIG. 17 is a simplified flow chart illustrating a variation of a method of making an elastic composite having dual elasticized regions, according to the present invention.
Figure 18:
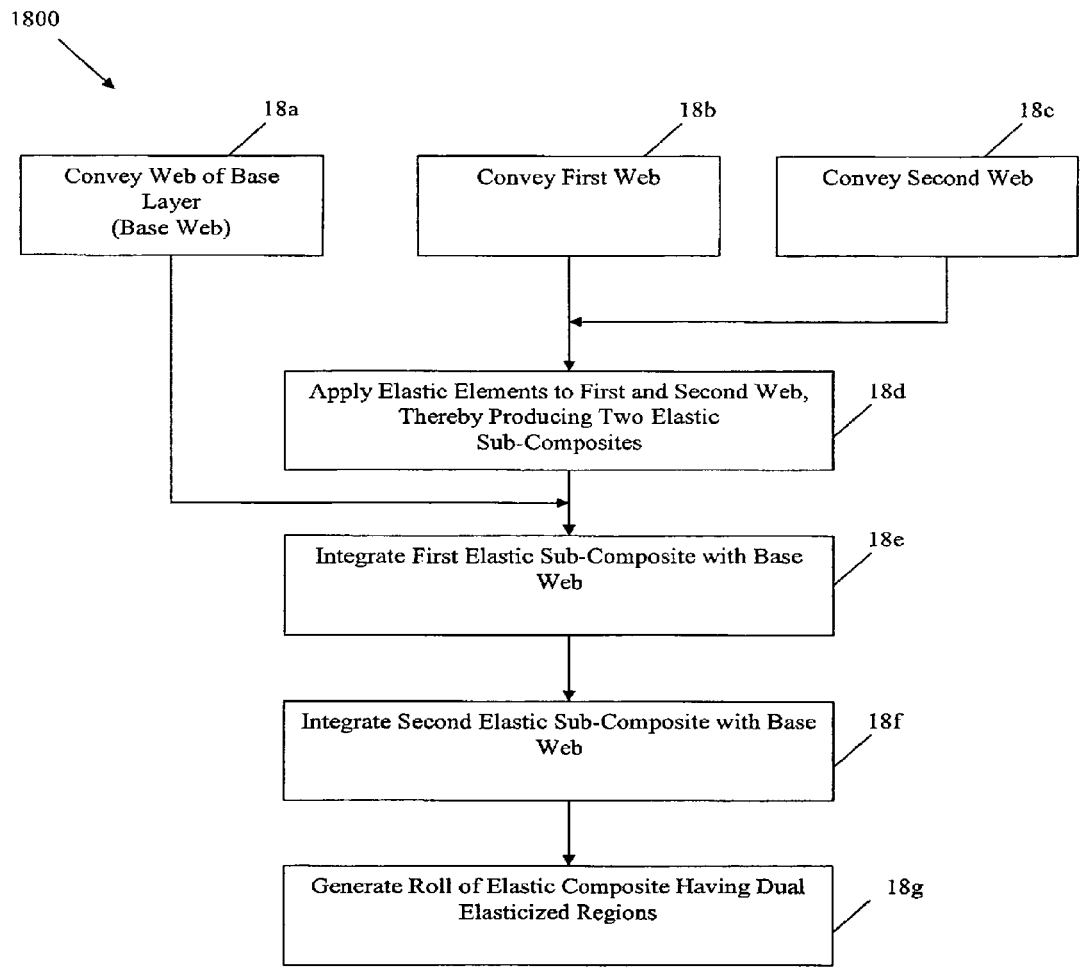
FIG. 18 is a simplified flow chart illustrating an exemplary method of making an elastic composite having dual elasticized regions, according to the present invention.

FIGS. 17 and 18 illustrate further and exemplary variations of the method described by the process of FIG. 16. Referring to the simplified flow chart 1700 of FIG. 17, in this embodiment, an initial step 17a of the process requires the conveyance of a web of a top layer (e.g., a narrow web of non-woven material). Next, the elastic elements are applied about or to the first web to produce a first elastic sub-composite (Step 17b). A web of the base layer (base web) is also conveyed (Step 17c) preferably toward a central integrating assembly. This first elastic sub-composite is then integrated with the base web (which is being conveyed) (Step 17d). This generates a larger web or web substrate having a single elasticized region thereon.

In this preferred embodiment, a second web of a top layer is conveyed (Step 17e). Elastic elements are applied about or to this second web to produce a second elastic sub-composite (Step 17f). This second elastic sub-composite is then integrated with the base web to produce an elastic composite having dual elasticized regions (Step 17g). Preferably, the second elastic sub-composite is applied such that the second elastic sub-composite is spaced apart from the first elastic sub-composite, thereby creating a central non-elasticized region therebetween. The central non-elasticized region includes the imaginary longitudinal centerline along which the elastic composite may be cut to produce two separate webs of elastic composites (having single elasticized regions).

Figure 19:
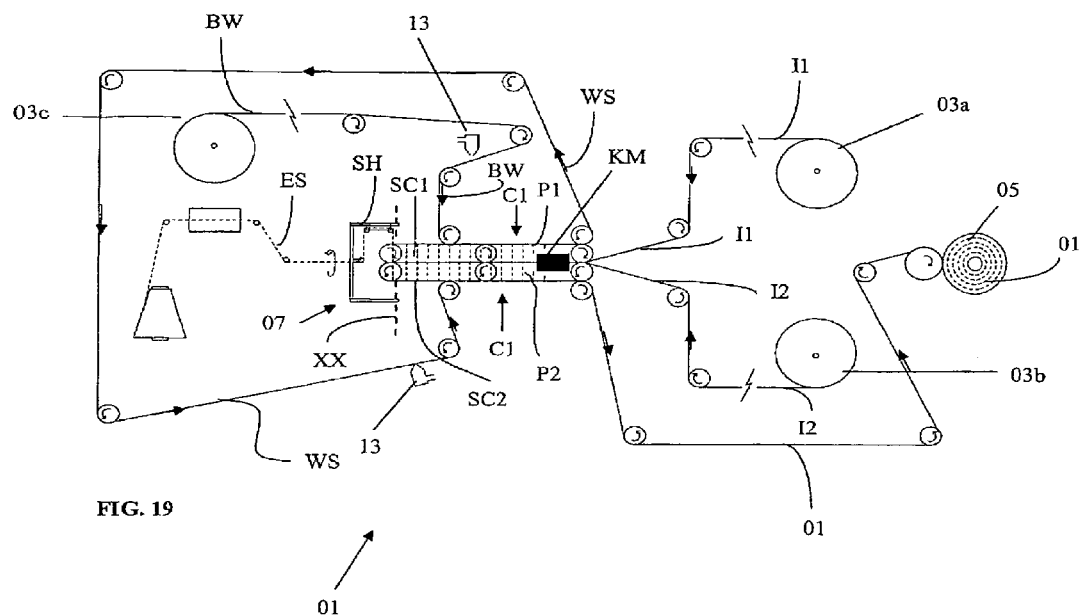
FIG. 19 is a simplified schematic of a system for manufacturing the elastic composite, according to the present invention.
Figure 20:
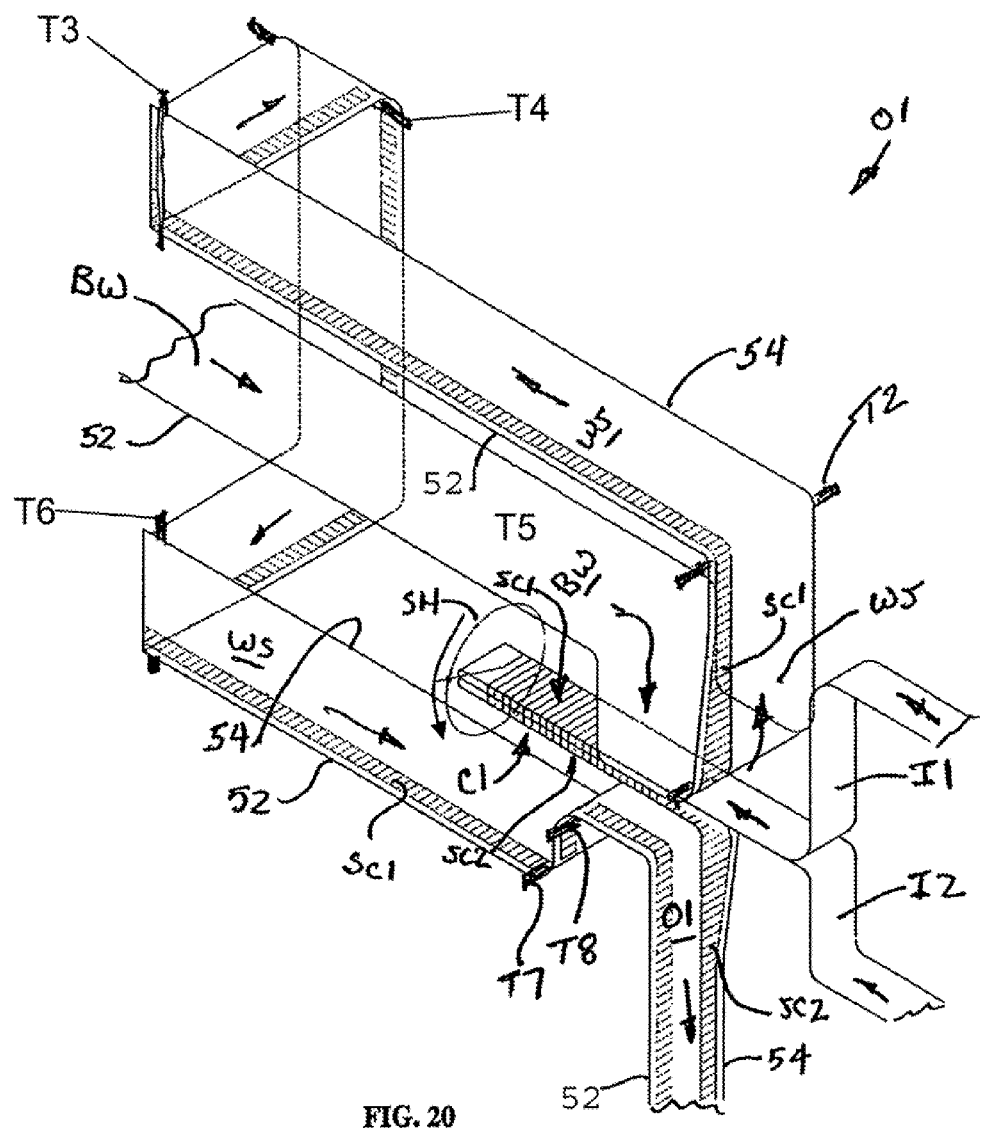
FIG. 20 is a simplified process illustration of a portion of the system in FIG. 19.

FIG. 18 illustrates yet another exemplary variation of the inventive method of making the elastic composite in the form of a simplified process flow chart 1800, according to the invention. References to the simplified flow chart 1800, and more particularly, the steps of the method, are made in describing a system O1 of making an elastic composite (having dual elasticized regions) according to the invention. The system O1 is illustrated in FIGS. 19 and 20.

The system O1 according to the present invention includes two input assemblies or reels 03a and 03b that each delivers a non-woven input web I1, I2. This exemplary system 01 further includes a third input assembly or reel 03c for delivering a web of a non-woven base layer (base web BW). Further yet, the system 01 employs an output assembly or reel 05 that receives or gathers a web (O1) of an elastic composite having dual elasticized regions, according to the present invention. The output web O1 is equivalent to the webs O1 previously described in respect to FIGS. 14 and 14A. These output webs O1 may further serve as input to a system of manufacturing a disposable absorbent garment.

Central to the system 01 is a conveyor assembly C1 for receiving, manipulating, and conveying, among other things, each of the non-woven input webs I1, I2. The conveyor assembly C1 includes a top conveyor platform P1 and a bottom conveyor platform P2 for moving the input webs I1, I2. The conveyor assembly C1 is positioned and operably associated with an elastic element applicator such as a spinning head assembly 07. The spinning head assembly 07 applies elastic fibers or strands upon, onto, and or integrally with the non-woven web inputs I1, I2. The spinning head assembly 07 further includes a spinhead SH, preferably in the form of a spinning bracket or cylinder SH. The spin cylinder SH is configured to hold an end section of the continuous strand ES of elastic and move the elastic strand ES about a generally vertical plane XX in a reciprocal or repetitive pattern, as previously described. Generally, the system and method according to the invention employs a conveyor assembly C1, a spinhead SH, and other system components familiar to those skilled in the relevant consumer product or manufacturing art, or other relevant art. Thus, details on the structure and operation of these system components are not included in the present description (but may be easily accessed from present reference materials, including the two patent publications previously referenced herein).

In initial steps (18a, 18b) of the inventive method, the conveyor assembly C1 preferably conveys and guides the non-woven input webs I1, I2 between the platforms P1, P2 toward the spinhead SH and then, within the spinning path XX of the spinhead SH. Once inside the spinning path XX, the conveyor assembly C1 delivers the non-woven web I1 to the upper face (outward faces) of the top conveyor platform P1 and non-woven web I2 to the lower face (outward face) of the bottom conveyor platform P2. At this stage, the directions of travel of the input webs I1, I2 are reversed and the webs I1, I2 are directed out of, and away from, the spinhead SH. As the input webs I1, I2 exit the spinhead SH, the elastic strand ES is wrapped about both platforms, and as the strand ES contacts the upper and lower face of the web platforms P1, P2, the strand ES comes into contact with the non-woven input webs I1,I2 moving thereon.

In this step 18d of the inventive process, the elastic strand ES is applied preferably cross-wise or laterally onto the webs I1, I2. The elastic strand evolves into an elastic construction on the non-woven web I1, I2. The result is an elastic sub-composite SC1 or SC2 provided by the engagement of a non-woven input web with the elastic elements of the elastic strand, as already disclosed in the prior art.

Referring also to FIG. 19, a third input reel 03 delivers a web of non-woven base layer or base web BW (Step 18a). In this embodiment, as illustrated in FIGS. 19 and 20, this base web BW is directed toward the top platform P1 of the conveyor assembly C1 via a series of rollers. The base web BW has a first side edge 52 and a second side edge 54. The path of the base web BW also takes it through an adhesive applicator 13 that applies adhesive on the inside surface of the base web BW and along a section close to the first side edge 52. As shown in FIG. 20, the base web BW is purposely made wider than the narrower non-woven input webs I1, I2. The path of the top elastic sub-composite SC1, converges with the path of the base web BW on the top platform P1, and more particularly, along the first side edge 52 of the base web BW at which adhesive is applied. The sub-composite SC1 and the base web BW mutually engage on the outside surface of the platform P1, thereby integrating the sub-composite SC1 with the base web BW (Step 18e). In this embodiment, the resulting combination (SC1 and BW) is conveyed together a short distance by the platform P1 and directed toward a knife mechanism KM. The knife mechanism KM severs the elastic strand to produce discrete and independent elastic elements.

Accordingly, a web substrate WS is generated composed of a wide base layer BW of non-woven and an elastic sub-composite SC1 positioned proximate the first side edge 52. The sub-composite SC1 provides an elastic construction of a plurality of spaced apart elastic elements that extend generally in the lateral direction and are disposed in generally parallel relation. In this embodiment, the input web or top layer I1 extends only slightly past the lateral extent of the elastic elements. Further, the elastic sub-composite SC1 is spaced inwardly from the first side edge 52 to provide a single layer, non-elasticized region between the sub-composite SC1 and the side edge 52.

Referring also to FIG. 20, the web substrate WS is directed away from the top platform P1 and directed through a series of turns that ultimately delivers the web substrate WS adjacent the bottom platform P2. It should be noted that FIG. 20 provides only a representative illustration of a path that the web substrate WS may take to arrive at the bottom platform P2. In this specific representation, the web substrate WS is first directed upwardly away from the top platform P1 and then makes a series of eight turns (T1 through T8) with the help of rollers and tension guides (represented as T1-T8) (or equivalent). Along the way, the web substrate WS passes through a second adhesive applicator 13 (See FIG. 19). At this juncture, adhesive is applied proximate the second side edge 54 of the base web BW away from the first sub-composite SC1. With reference particularly to FIG. 20, after turn T8, the web substrate WS moves along the same direction as the reverse direction of the conveyor assembly C1 (away from the spinhead SH) but positioned below the bottom conveyor platform P2. Furthermore, at this stage and position, the web substrate WS is not directly aligned or centered with the conveyor platforms P1, P2, but positioned laterally askew from the longitudinal centerline of the conveyor platforms P1, P2. As a result, the wider web substrate WS presents only a section near the second side edge 54 directly below the conveyor platform P2. This section or overlap can directly engage the platform P2.

As indicated in FIGS. 19 and 20, a second sub-composite SC2 is moved by the bottom platform P2 into direct engagement with the approaching web substrate WS. The second sub-composite SC2 is integrated with the web substrate WS in the same manner as the first sub-composite SC1 (Step 18o. Thus, the second sub-composite SC2 is applied proximate the second side edge 54 of the base web BW. The bottom platform P2 moves the resulting combination web O1 of non-woven layers and elastic construction away from the spinhead SH and toward the knife mechanism KM.

As a result, a new multi-component web O1 of elastic composite is generated. According to the present invention, the web O1 of an elastic composite includes a base web BW and dual elastic sub-composites SC1, SC2, and dual elasticized regions proximate the first and second side edges 52, 54, respectively. The sub-composites SC1, SC2 are laterally spaced apart to define a single layer, non-elasticized region therebetween. In this specific embodiment, the sub-composites SC1, SC2, and, more particularly, the elastic elements and top non-woven layers that compose the sub-composites SC1, SC2, are also spaced inwardly from the first and second sides edges of the base layer, thereby defining a single layer, a non-elasticized region along each side edge.

In a subsequent step 18g of the inventive method, this web O1 of elastic composite is directed by series of rollers to the output reel 05 and gathered as a roll. The web or roll O1 on the output reel 05 may be removed when full. The roll O1 may also be delivered directly to a knife mechanism KM, whereupon it is converted to two strips of single elasticized composites. Furthermore, the output web O1 may be directed to a larger system for manufacturing disposable absorbent garments.

It should be noted that the directions and turns through which the web substrate is directed, as discussed above, may be changed in alternative embodiments. The specific paths illustrated in FIGS. 19 and 20 are, in fact, representative and do not correspond exactly with any specific physical arrangement. The path illustrated in FIGS. 19 and 20 are provided only for exemplary purposes. Furthermore, in other embodiments, the base web BW and input reel 03c may be provided near the bottom platform P2, and thus, first directed toward the bottom platform P2 rather than the top platform P1. In such an embodiment, the resulting web substrate WS is directed through a series of turns that ultimately positions the web substrate WS adjacent the top platform P1, whereupon the sub-composite SC1 is integrated with the web substrate WS.

In another embodiment, the system and method provides, in lieu of two narrow input webs I1, I2, a single input web may be provided from a single source or spool. This single non-woven input web has a width that is generally twice the width of the narrow input webs I1, I2. This wider web may then be split prior to delivery to the conveyor, so as to provide the two narrow input webs (e.g., I1, I2) discussed above.

Figure 21:
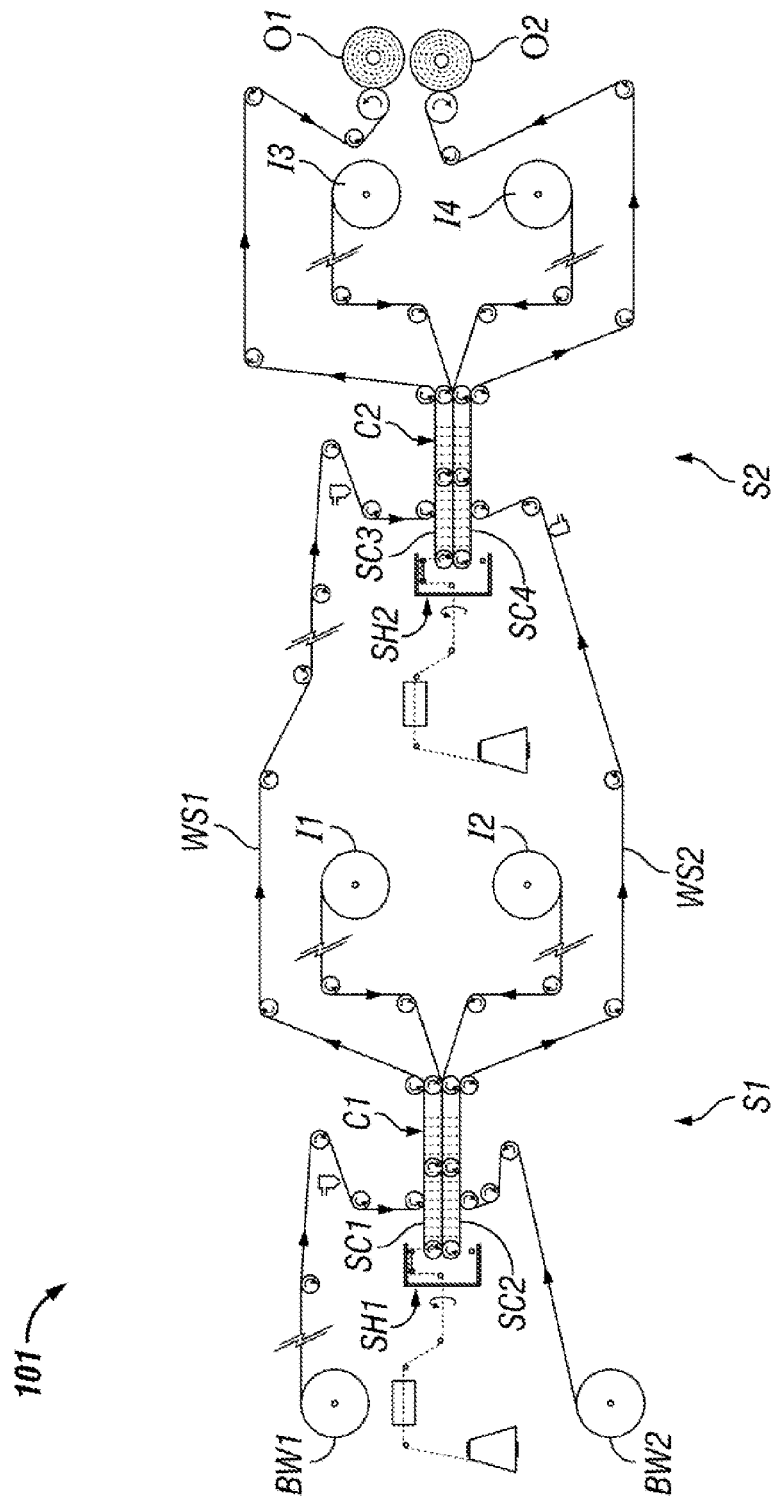
FIG. 21 is a simplified schematic of an alternative system for manufacturing the elastic composite, according to the present invention.

FIG. 21 provides yet another alternative system 101 of making an elastic composite having dual elasticized regions, according to the present invention. FIG. 21 also reveals an alternate method for making the inventive elastic composite. In this alternate system 101, the system 101 may be characterized as having a first sub-system S1 and a second sub-system S2 in series with the first sub-system S1. The first sub-system S1 is to the left of the second sub-system S2 in the illustration of FIG. 21, and as will be revealed below S2, is downstream of sub-system S1 in the exemplary process.

Each sub-system S1, S2 employs a conveyor assembly C1, C2, and a spinhead SH1, SH2. In contrast to the previously described system O1, this system 101 employs two input assemblies or reels for delivering a base web BW1, BW2. Furthermore, the system 101 requires two non-woven input webs (I1, I2; I3, I4) for each of the sub-systems S1, S2. As a result, the system and method according to this embodiment, generates two output webs O1, O2 of the elastic composite.

First, input webs I1 and I2 are delivered into conveyor C1. The spinhead SH1 applies a continuous elastic strand about the moving input webs I1, I2, thereby generating sub-composites SC1, SC2. In this embodiment, base webs BW1 and BW2 are applied to the top and bottom platforms of the conveyor assembly C1, respectively, and engage the sub-composites SC1, SC2, respectively. Engagement of the base webs BW1, BW2 and the sub-composites SC1, SC2, delivers two separate web substrates WS1, WS2. In this embodiment, the movement of input webs I1, I2, the generation of sub-composites SC1, SC2, and the delivery of web substrates WS1, WS2 are preferably performed simultaneously. Thus, the output result of the first sub-system S1 are two separate web substrates WS1, WS2 composed of a base web and an elastic sub-composite applied to one of two side edges of the base web BW1, BW2.

As shown in FIG. 21, both web substrates WS1, WS2 are then directed downstream into sub-system S2. In sub-system S2, non-woven input webs I3, I4, are also moved into the conveyor assembly C2 and the spinhead SH2. Each of the input webs I3, I4 is generally of the same width as the narrow input webs I1, I2 (in sub-system S1). As before, the spinhead SH2 operates to apply elastic elements on the input webs I3, I4, thereby generating a third and fourth elastic sub-composite SC3, SC4. Web substrates WS1, WS2 which are outputs of sub-system S1, are then directed to the top and bottom platforms, respectively, of the conveyor assembly C2. Before reaching the conveyor assembly C2, the section of web substrate WS1, WS2 adjacent the bare side edge (opposite of SC1, SC2) is passed through another adhesive applicator and provided with adhesive. This section adjacent the side edge then is brought into contact with the sub-composite SC3, SC4 on the conveyor platforms. The sub-composite SC3, SC4 merges along the second side edge of the web substrate WS1 or WS2. As a result, a web O1, 02 of the elastic composite is generated and delivered as output of the conveyor assembly C2. The two webs O1, O2 of the elastic composites is then directed to an output reel and gathered.

In further variations of the system of FIG. 21, multiple additional sub-systems may be provided downstream of, and in series with, sub-systems S1, S2. In such embodiments, the widths of the base webs and input webs may be varied to accommodate multiple elasticized regions of an elastic composite. Further, in these embodiments, the conveyor assemblies and rollers are located to precisely position each incoming web substrate for engagement with an additional sub-composite.

The foregoing description of the present invention has been presented for purposes of illustration and description. It is to be noted that the description is not intended to limit the invention to the various systems, apparatus, and processes disclosed herein. Various aspects of the invention, as described above, may be applicable to other types of disposable absorbent articles, garments, and the like, and processes for making the same. For example, the elastic composite described above, may be incorporated in other disposable absorbent garments such as training pants, etc. or in other areas or as other components of the garment. The elastic composite may also be incorporated into or with other garments, textiles, fabrics, and the like, or combinations thereof. Moreover, the various aspects of the process described in respect to FIGS. 19-21 may be utilized to produce compositions, garments and articles other than those described herein. Such variations of the invention will become apparent to one skilled in the relevant consumer products art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. An elastic composite for use in manufacturing disposable absorbent garments, the elastic composite comprising:
   a base layer having a pair of side edges and a longitudinal centerline spaced inwardly from the side edges;
   a first elastic construction adhered to the base layer, the first elastic construction including a first plurality of spaced apart elastic elements;
   a first top layer extending over the first elastic construction;
   a second elastic construction adhered to the base layer, the second elastic construction including a second plurality of spaced apart elastic elements; and
   a second top layer extending over the second elastic construction;
   wherein the first and second top layers and the first and second elastic constructions are spaced apart to define a single-layer central non-elasticized region between the first and second elastic constructions; and
   wherein at least one of the first plurality of spaced apart elastic elements and at least one of the second plurality of spaced apart elastic elements extend laterally from the central non-elasticized region.

2. The elastic composite of claim 1, wherein the first and second top layers are spaced apart to define a seamless non-elasticized region formed by the base layer.

3. The elastic composite of claim 1, wherein the first plurality of elastic elements are spaced inwardly from the first side edge to form a first non-elasticized region therebetween, and the second plurality of elastic elements are spaced inwardly from the second side edge to form a second non-elasticized region therebetween.

4. The elastic composite of claim 3, wherein the first and second top layers are spaced inwardly from the first and second side edges, respectively, to define single-layer first and second non-elasticized regions.

5. The elastic composite of claim 1, wherein the elastic elements in the first and second elastic constructions are disposed generally transverse to the longitudinal centerline and in mutual generally parallel relation.

6. An elastic composite for use in manufacturing disposable absorbent garments, the elastic composite comprising:
   a base layer;
   a first elastic sub-composite adhered to the base layer, the first elastic sub-composite having a first plurality of spaced apart elastic elements disposed in generally parallel relation and a top layer extending over the first plurality of elastic elements; and
   a second elastic sub-composite adhered to the base layer, the second elastic sub-composite having a second plurality of spaced apart elastic elements disposed in generally parallel relation and a top layer extending over the second plurality of elastic elements; and
   wherein the first and second sub-composites are spaced apart to define a single-layer central non-elasticized region therebetween; and
   wherein the first plurality of spaced apart elastic elements and the second plurality of spaced apart elastic elements extend laterally from the central non-elasticized region.

7. The elastic composite of claim 6, wherein the first and second sub-composites are spaced apart to define a seamless central non-elasticized region formed by the base layer.

8. The elastic composite of claim 7, wherein the base layer includes a first side edge and a second side edge, the first plurality of elastic elements being spaced inwardly from the first side edge to form a first non-elasticized region therebetween, and the second plurality of elastic elements being spaced inwardly from the second side edge to form a second non-elasticized region therebetween.

9. The elastic composite of claim 8, wherein the first and second non-elasticized region consists of a single material layer provided by the base layer.

10. The elastic composite of claim 6, wherein the elastic elements extends generally in the cross-machine direction.

11. The elastic composite of claim 6, wherein each of the top layers extends laterally proximate the lateral extent of the elastic elements of the elastic sub-composites.

* * * * *

UNITED STATES PATENT AND TRADEMARK OFFICE
CERTIFICATE OF CORRECTION

| | | |
|---|---|---|
| PATENT NO. | : 8,822,015 B1 | Page 1 of 1 |
| APPLICATION NO. | : 12/069928 | |
| DATED | : September 2, 2014 | |
| INVENTOR(S) | : Ottery et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 871 days.

Signed and Sealed this
Fifteenth Day of December, 2015

Michelle K. Lee
*Director of the United States Patent and Trademark Office*